United States Patent [19]

Yamamoto et al.

[11] Patent Number: 5,326,857
[45] Date of Patent: Jul. 5, 1994

[54] ABO GENOTYPING

[75] Inventors: Fumi-ichiro Yamamoto, Bellevue; Thayer White, Seattle; Sen-itiroh Hakomori, Mercer Island, all of Wash.; Henrik Clausen, Holte, Denmark

[73] Assignee: The Biomembrane Institute, Seattle, Wash.

[21] Appl. No.: 752,101

[22] Filed: Aug. 29, 1991

Related U.S. Application Data

[63] Continuation-in-part of Ser. No. 402,695, Aug. 31, 1989, Pat. No. 5,068,191.

[51] Int. Cl.$^5$ .................. C07H 21/02; C12N 15/70; C12N 5/10
[52] U.S. Cl. ................ 536/23.2; 435/320.1; 435/240.2; 536/23.1
[58] Field of Search ............ 435/240.1, 252.3, 320.1, 435/193; 536/26–29, 23.1

[56] References Cited

PUBLICATIONS

Childs et al., "Blood-group-related carbohydrate antigens are expressed on human milk galactosyltransferase and are immunogenic in rabbits," *Biochem. J.* 238:604–611 (1986).

Clausen et al., "Monoclonal Antibodies Defining Blood Group A Variants with Difucosyl Type 1 Chain (ALe$^y$)," *Biochemistry* 24:6190–6194 (1985).

Clausen et al., "Further Characterization of Type 2 and Type 3 Chain Blood Group A Glycosphingolipids from Human Erythrocyte Membranes," *Biochemistry* 25:7075–7085 (1986).

Clausen et al., "Incompatible A Antigen Expressed in Tumors of Blood Group O Individuals: Immunochemical, Immunohistologic, and Enzymatic Characterization," *J. Immunol* 136:326–330 (1986).

Cook et al., "A rabbit antibody to the blood-group-A-gene-specified a-3-N-acetylgalactosaminyl-transferase," *Bio-chem. Soc. Trans.* 10:446–447 (1982).

Greenwell et al., "Approaches to cloning the genes at the human blood group ABO locus," *Biochem. Soc. Trans.* 15:601–603 (1987).

Nagai et al., "Human Blood Group Glycosyltransferases," *J. Biol. Chem.* 253:377–379 (1978).

Roth et al., "Differential Subcompartmentation of Terminal Glycosylation in the Golgi Apparatus of Intestinal Absorptive and Goblet Cells," *J. Biol. Chem.* 261:14307–14312 (1986).

Schwyzer et al., "Porcine A Blood Group-specific N-Acetylgalactosaminyltransferase," *J. Biol. Chem.* 252:2346–2355 (1977).

Taatjes et al., "Post-Golgi Apparatus Localization and Regional Expression of Rat Intestingal Sialytransferase Detected by Immunoelectron Microscopy with Polypeptide Epitope-purified Antibody," *J. Biol. Chem.* 263:6302–6309 (1988).

Takizawa et al., "Immunological Specificity of Blood Group Glycosyltransferase," in T. Yamakawa, T. Osawa and S. Handa (eds.), *Glycoconjugates*, Japanese Scientific Societies Press, Tokyo, 1981, pp. 379–380.

Topping et al., "Isoelectric Points of the Human Blood Group A$^1$, A$^2$ and B Gene-Associated Glycosyltransferases in Ovarian Cyst Fluids and Serum," *Biochem. Biophys. Res. Commun.* 64:89–96 (1975).

(List continued on next page.)

Primary Examiner—Margaret Parr
Assistant Examiner—Stephanie W. Zitomer
Attorney, Agent, or Firm—Seed and Berry

[57] ABSTRACT

The genes defining the ABO histo-blood groups are disclosed. Methods for identification of histo-blood group ABO status are provided. The methods include the use of DNA probes or size separation of DNA fragments unique to a blood group status. The present invention also discloses DNA constructs, recombinant methods for providing histo-blood glycosyltransferases, methods for tumor suppression, purified histo-blood group glycosyltransferases, and antibodies produced therefrom which bind to protein epitopes.

30 Claims, 16 Drawing Sheets

OTHER PUBLICATIONS

Tuppy et al., "Microsomal Incorporation of N-Acetyl-D-Galactosamine into Blood Group Substance," *Nature* 210:316–317 (1966).

Watkins et al., "Specific Inhibition Studies Relating to the Lewis Blood-Group System," *Nature* 180:1038–1040 (1957).

Watkins et al., "Possible Genetical Pathways for the Biosynthesis of Blood Group Mucopolysaccharides," *Vox Sang.* 4:97–119 (1959).

Whitehead et al., "An N-acetylgalactosaminyl-transferase From Human Blood Group A Plasma," *J. Biol. Chem.* 249:3442–3447 (1974).

Yoshida et al., "Immunologic Homology of Human Blood Group Glycosyltransferases and Genetic Background of Blood Group (ABO) Determination," *Blood* 54:344–350 (1979).

Yoshida, "Identification of Genotypes of Blood Group A and B," *Blood* 55:119–123 (1980).

a.

```
                             5                        10                      15
   (Lys) asp Glu Gly his   Phe Tyr Tyr Leu Gly Gly Phe Phe Gly Gly
                  5'                                              3'
        Oligo FY-1:  TTC TAC TAC CTG GGA GGA TTC TTC GG
                      T   T   T   C   C   C   T   T
                                  T   T
```

```
               20              25
   Ser Val Gln Glu Val Gln Arg Leu Thr Arg Ala gln
                                              cys
          5'                  3'
   FY-3:  GTG CAG GAG GTG CAG AG
           A   A   A   A   A C
           C           C
           T           T
```

```
               30              35              40
   xxx Gln Ala Met Met Val Asp Gln Ala asn Gly Ile Glu Ala Val
                T                     T
            T   A           C   A     A
           GTC CGG TAC TAC CAG CTG GTC CGG TTG CC : FY-2
         3'                                       5'
``` b.    c.

1  2  3  4      5  6  7  8  9  10  11

118 bp—

72 bp—                                     —98 bp

```
  1  ATG GCC GAG GTG TTG CGG ACG CTG GCC GGA AAA CCA AAA TGC CAC
  1  met ala glu val leu arg thr leu ala gly lys pro lys cys his 46  GCA CTT CGA CCT ATG ATC CTT TTC CTA ATA ATG CTT GTC TTG GTC
 16  ala leu arg pro met ile leu phe leu ile met leu val leu val
                   <=========== possible transmembrane domain ============

91  TTG TTT GGT TAC GGG GTC CTA AGC CCC AGA AGT CTA ATG CCA GGA
 31  leu phe gly tyr gly val leu ser pro arg ser leu met pro gly
     ===================>

136  AGC CTG GAA CGG GGG TTC TGC ATG GCT GTT AGG GAA CCT GAC CAT
 46  ser leu glu arg gly phe cys met ALA val arg glu pro asp his
                                    <--  --- --- --- --- --- ---

181  CTG CAG CGC GTC TCG TTG CCA AGG ATG GTC TAC CCC CAG CCA AAG
 61  leu gln arg val ser leu pro arg met val tyr pro gln pro lys
     --- M-9/K-4 --- --- --- --- --- --- --- --- --- xxx <-->

226  GTG CTG ACA CCG TGG AAG GAT GTC CTC GTG GTG ACC CCT TGG CTG
 76  val leu thr pro TRP lys ASP val leu val val thr pro trp leu
     --- K-1 --- --cys xxx<> arg --- K-9 --- --->

271  GCT CCC ATT GTC TGG GAG GGC ACA TTC AAC ATC GAC ATC CTC AAC
 91  ala pro ile val trp glu gly thr phe asn ile asp ile leu asn 316  GAG CAG TTC AGG CTC CAG AAC ACC ATT GGG TTA ACT GTG TTT
106  glu gln phe arg leu gln ASN thr thr ile gly leu thr val phe 361  GCC ATC AAG AAA TAC GTG GCT TTC CTG AAG CTG TTC CTG GAG ACG
121  ala ile lys lys tyr val ala phe leu lys leu phe leu glu thr
```

*FIG. 3A*

```
406  GCG GAG AAG CAC TTC ATG GTG GGC CAC CGT GTC CAC TAC TAT GTC
136  ala glu lys HIS phe met val gly his arg val his tyr tyr val
                 <-- ASP ---           --- K-5/M-7 ---

451  TTC ACC GAC CAG CTG GCC GCG GTG CCC CGC GTG ACG CTG GGG ACC
151  phe thr asp gln LEU ala ala val pro arg val thr leu gly thr
                 --- PRO ---

496  GGT CGG CAG CTG TCA GTG CTG GAG GTG CGC GCC TAC AAG CGC TGG
166  gly arg gln leu ser val leu glu val arg ala tyr lys arg trp 541  CAG GAC GTG TCC ATG CGC ATG GAG ATG ATC AGT GAC TTC TGC
181  gln asp val ser met arg met glu met ile ser asp phe cys
                                             --- M-8 --->

586  GAG CGG CGC TTC CTC AGC GAG GTG GAT TAC CTG TGC GTG GAC
196  glu arg arg phe leu ser glu val asp tyr leu cys val asp
                                                         --^

631  GTG GAC ATG GAG TTC CGC GAC CAC CCC GTG GGC GTG ATC CTG ACT
211  val asp met glu phe arg asp his pro val gly val ile leu thr 676  CCG CTG TTC GGC ACC CTG CAC CCC GGC TTC TAC GGA AGC AGC CGG
226  pro leu phe gly thr leu his pro gly phe tyr gly ser ser arg 721  GAG GCC TTC ACC TAC GAG CGG CGG CCC CAG TCC CAG GCC TAC ATC
241  glu ala phe thr tyr glu arg arg pro gln ser gln ala tyr ile 766  CCC AAG GAC GAG GGC GAT TTC TAC TAC CTG TAC TAC GGG TTC TTC GGG
256  pro lys asp glu gly ASP phe tyr tyr leu tyr tyr gly phe phe gly
```

FIG. 3B

```
811  GGG  <--  ---  ---  ---  ---  ---  --- K-8 ---  ---  ---  ---  ---  ---  ---
271  gly  <--  ---  ---  ---  ---  ---  --- his ---  ---  ---  ---  ---  ---  ---

TCG  GTG  CAA  GAG  GTG  CAG  CGG  CTC  ACC  AGG  GCC  TGC  CAC  CAG
     ser  val  gln  glu  val  gln  arg  leu  thr  arg  ala  cys  his  gln
                                                            ---  xxx  ---  ---

856  GCC  ATG  ATG  GTC  GAC  CAG  GCC  AAC  GGC  ATC  GAG  GCC  GTG  TGG  CAC
286  ala  met  met  val  asp  gln  ala  asn  gly  ile  glu  ala  val  trp  his
                                                                      --->

901  GAC  GAG  AGC  CAC  CTG  AAC  CTG  CTG  TAC  CTG  CGC  CAC  AAA  CCC  ACC
301  asp  glu  ser  his  leu  asn  leu  leu  tyr  leu  arg  his  lys  pro  thr
                              <-- K-2 ---

946  AAG  GTG  CTC  TCC  CCC  GAG  TAC  TTG  TGG  GAC  CAG  CAG  CTG  CTG  GGC
316  lys  val  leu  ser  pro  glu  tyr  leu  trp  asp  gln  gln  leu  leu  gly
     <--> K-7 ---                                             ---  xxx  ---  ---

991  TGG  CCC  GCC  GTC  GTC  AGG  AAG  CTG  AGG  TTC  ACT  GCG  GTG  CCC  AAG
331  trp  pro  ala  val  val  arg  lys  leu  arg  phe  thr  ala  val  pro  lys
                              ---  xxx  <--> K-3 ---                      --->

1036 AAC  CAC  CAG  GCG  GTC  CGG  AAC  CCG  TGA
346  asn  his  gln  ala  val  arg  asn  pro  ---
```

FIG. 3C

```
                  10         20         30         40         50
FY-59-A   MAEVLRTLAG KPKCHALRPM ILFLIMLVLV LFGYGVLSPR SLMPGSLERG
FY-65-O   ?????????? ********** ********** ********** **********
FY-66-A   ********** ********** ********** ********** **********
FY-66-B   ********** ********** ********** ********** **********
FY-68-O   ?********* ********** ********** ******F*** **********
FY-69-B   ?********* ********** ********** ********** **********
FY-69-O   ?********* ********** ********** ********** **********

60         70         80         90         100
FY-59-A   FCMAVREPDH LQRVSLPRMV YPQPKVLTPW KDVLVVTPWL APIWEGTFN
FY-65-O   ******** ****** ****** CR**** PLGW****
FY-66-A   ******** ****** ****** CR****** LPLSGRAHST
FY-66-B   ******** ****** ****** CR**** ********
FY-68-O   ******** H* *S CR****** PLGW LPLSGRARST
FY-69-B   ******** ****** ****** CR**** ********
FY-69-O   ******** ****** ****** CR****** PLGW LPLSGRAHST 110        120        130        140        150
FY-59-A   IDILNEQFRL QNTTIGLTVF AIKKYVAFLK LFLETAEKHF MVGHRVHYYV
FY-65-O   STSSTSSSGS RTPPLG- ********** ********** **********
FY-66-A   ********** ********** ********** ********** **********
FY-66-B   ********** ********** ********** ********** **********
FY-68-O   STSSTSSSGS RTPPLG-
FY-69-B   ********** ********** ********** ********** **********
FY-69-O   STSSTSSSGS RTPPLG-
```

FIG. 5A

```
              160        170        180        190        200
FY-59-A   FTDQLAAVPR VTLGTGRQLS VLEVRAYKRW QDVSMRRMEM ISDFCERRFL
FY-65-O   ********** ********** ********** ********** **********
FY-66-A   ****P***** ********** ********** ********** **********
FY-66-B   ****P***** ********** ****G***** ********** **********
FY-68-O   ********** ********** ********** ********** **********
FY-69-B   ****P***** ********** ****G***** ********** **********
FY-69-O   ********** ********** ********** ********** **********

210        220        230        240        250
FY-59-A   SEVDYLVCVD VDMEFRDHVG VEILTPLFGT LHPGFYGSSR EAFTEYRRPQ
FY-65-O   ********** ********** ********** ********** **********
FY-66-A   ********** ********** ********** ********** **********
FY-66-B   ********** ********** ********** ****S***** **********
FY-68-O   ********** ********** ********** ********** **********
FY-69-B   ********** ********** ********** ****S***** **********
FY-69-O   ********** ********** ********** ********** **********

260        270        280        290        300
FY-59-A   SQAYIPKDEG DFYYLGGFFG GSVQEVQRLT RACHQAMMVD QANGIEAVWH
FY-65-O   ********** ********** ********** ********** **********
FY-66-A   ********** ********** ********** ********** **********
FY-66-B   ********** ****M*A*** ********** ********** **********
FY-68-O   ********** ********** ********** ********** **********
FY-69-B   ********** ****M*A*** ********** ********** **********
FY-69-O   ********** ********** ********** ********** **********
```

FIG. 5B

```
                 310        320        330        340        350
              |         |          |          |          |
FY-59-A   DESHLNKYLL RHKPTKVLSP EYLWDQQLLG WPAVLRKLRF TAVPKNHQAV
FY-65-O
FY-66-A   ********** ********** ********** ********** **********
FY-66-B   ********** ********** ********** ********** **********
FY-68-O
FY-69-B   ********** ********** ********** ********** **********
FY-69-O

360
FY-59-A   RNP-
FY-65-O
FY-66-A   ****
FY-66-B   ****
FY-68-O
FY-69-B   ****
FY-69-O
```

FIG. 5C

|  |  | BstE II | |
|---|---|---|---|
| 59A,66-A,66-B,69-B | 252 | C G T G G T G A C C C T T | |
| 65-0,68-0,69-0 |  | C G T G G T - A C C C T T | |
|  |  | KpnI | |

|  |  | Bss H II | |
|---|---|---|---|
| 59-A,65-0,66-A,68-0,69-0 | 517 | G A G G T G C G C G C C T | |
| 66-B,69-B |  | G A G G T G G G C G C C T | |
|  |  | NarI | |

|  |  | Hpa II | |
|---|---|---|---|
| 59-A,65-0,66-A,68-0,69-0 | 694 | C A C C C C G C T T C T T | |
| 66-B,69-B |  | C A C C C C A G C T T C T | |
|  |  | Alu I | |

|  |  | Bst NI | |
|---|---|---|---|
| 59-A,65-0,66-A,68-0,69-0 | 787 | T A C T A C C T G G G G G T T C T T | |
| 66-B,69-B |  | T A C T A C A T G G G G C G T T C T T | |
|  |  | Nla III | |

FIG. 6A

FIG. 6B
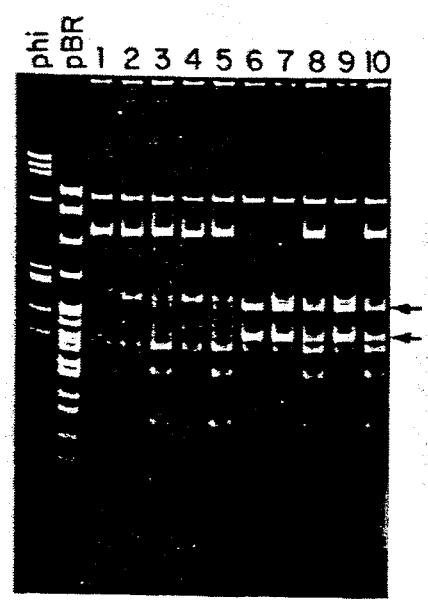
FIG. 6C
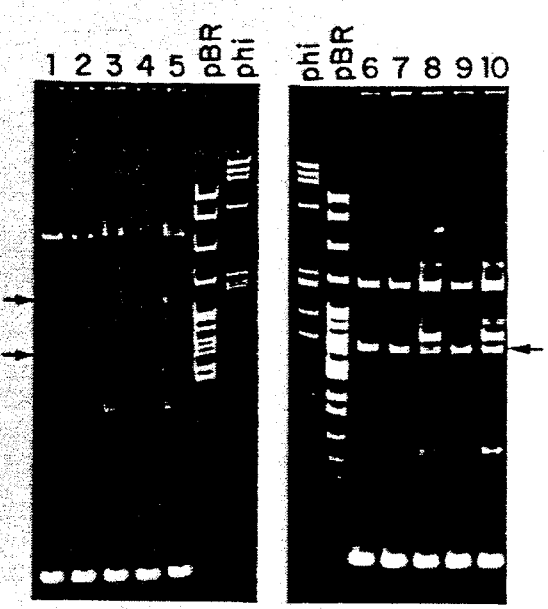
FIG. 6D

| | | |
|---|---|---|
| A1 | MAEVLRTLAGKPKCHALRPMILFLIMLVLVLFGYGVLSPR | 40 |
| A2 | ???????????????????????????????????????? | |
| | | |
| A1 | SLMPGSLERGFCMAVREPDHLQRVSLPRMVYPQPKVLTPC | 80 |
| A2 | ???????????\*\*\*\*\*\*\*\*\*\*\*\*\*\*\*\*\*\*\*\*\*\*\*\*\*\*\*\*\* | |
| | | |
| A1 | RKDVLVVTPWLAPIVWEGTFNIDILNEQFRLQNTTIGLTV | 120 |
| A2 | \*\*\*\*\*\*\*\*\*\*\*\*\*\*\*\*\*\*\*\*\*\*\*\*\*\*\*\*\*\*\*\*\*\*\*\*\*\*\*\* | |
| | | |
| A1 | FAIKKYVAFLKLFLETAEKHFMVGHRVHYYVFTDQPAAVP | 160 |
| A2 | \*\*\*\*\*\*\*\*\*\*\*\*\*\*\*\*\*\*\*\*\*\*\*\*\*\*\*\*\*\*\*\*\*\*L\*\*\*\* | |
| | | |
| A1 | RVTLGTGRQLSVLEVRAYKRWQDVSMRRMEMISDFCERRF | 200 |
| A2 | \*\*\*\*\*\*\*\*\*\*\*\*\*\*\*\*\*\*\*\*\*\*\*\*\*\*\*\*\*\*\*\*\*\*\*\*\*\*\*\* | |
| | | |
| A1 | LSEVDYLVCVDVDMEFRDHVGVEILTPLFGTLHPGFYGSS | 240 |
| A2 | \*\*\*\*\*\*\*\*\*\*\*\*\*\*\*\*\*\*\*\*\*\*\*\*\*\*\*\*\*\*\*\*\*\*\*\*\*\*\*\* | |
| | | |
| A1 | REAFTYERRPQSQAYIPKDEGDFYYLGGFFGGSVQEVQRL | 280 |
| A2 | \*\*\*\*\*\*\*\*\*\*\*\*\*\*\*\*\*\*\*\*\*\*\*\*\*\*\*\*\*\*\*\*\*\*\*\*\*\*\*\* | |
| | | |
| A1 | TRACHQAMMVDQANGIEAVWHDESHLNKYLLRHKPTKVLS | 320 |
| A2 | \*\*\*\*\*\*\*\*\*\*\*\*\*\*\*\*\*\*\*\*\*\*\*\*\*\*\*\*\*\*\*\*\*\*\*\*\*\*\*\* | |
| | | |
| A1 | PEYLWDQQLLGWPAVLRKLRFTAVPKNHQAVRNP= | 354 |
| A2 | \*\*\*\*\*\*\*\*\*\*\*\*\*\*\*\*\*\*\*\*\*\*\*\*\*\*\*\*\*\*\*\*\*\*\*\*RERLPGA | 360 |
| | | |
| A1 | | |
| A2 | LGGLPAAPSPSRPWF= | 375 |

FIG. 7

| | | |
|---|---|---|
| A1 | AACCACCAGGCGGTCCGGAACCCGTGAGCGGCT | 1071 |
| A2 | ********************************* | 1070 |
| A1 | N H Q A V R N P = | 354 |
| A2 | * * * * * * * R E R L | 357 |
| A1 | GCCAGGGGCTCTGGGAGGGCTGCCGGCAGCCCC | 1104 |
| A2 | ********************************* | 1103 |
| A1 | | |
| A2 | P G A L G G L P A A P | 368 |
| A1 | GTCCCCCTCCCGCCCTTGGTTTTAG | 1029 |
| A2 | ************************* | 1028 |
| A1 | | |
| A2 | S P S R P W F = | 375 |

```
                    PRIMER fy-81
              T C              T
       EcoRI /              /
   5' CGGAATTCAAGTACTTCATGGTGGGCCA
      * * ********** *****
bGal 457   AAGCACTTCATGGTGGGCCA....TGGCATGATGAAAGCCATCT   959
mGal 535   ATGTACTTCATGGTTGGCCA....TGGCATGATGAGAGCCACCT  1037
hGal 535'  AGGTACTTCATGGTTGGCCA....TGGCATGATGAAAGCCACCT  1035'
A    412   AAGCACTTCATGGTGGGCCA....TGGCACGACGAGAGCCACCT   914
                                  ***** ** ** ******
                              ACCGTGCTGCTTTCGGTGGACTTAAGGC 5'
                                   ^  ^   ^          / EcoRI
                                   A  A   C       ^
                                                  A
                                      PRIMER fy-82
```

FIG. 10A

```
hgt4                                                          ======
A     GTGGCT---TTCCTGAAGCTGTTCCTGGAGACGGCGGAGAAGCAC            417 hgt4
A      V  A  -  F  L  K  L  F  L  E  T  A  E  K  H          (139)
                 ** *           *    * hgt4  ===fy-81=====>TAGGGTGAACTACTACA-CTTCACCAACCAG           461'
A     TTCATGGTGGGCCACCGTGTCCACTACTATGTCTTCACCGACCAG           462
                               *        * hgt4                     R  V  N  Y  Y  /  F  T  N  Q
A      F  M  V  G  H  R  V  H  Y  Y  V  F  T  D  Q          (154)
          * **     *     *           *        * hgt4  CCAGGACACATTCCACACATCAAGCTCTGAGAGGGACGGCAGATG           506'
A     CTGGCCGCGGTGCCCCGCGTGACGCTGGGGACCGGTCGGCAGCTG           507
                  *               * hgt4   P  G  H  I  P  H  I  K  L ter E  G  R  Q  M
A      P  A  A  V  P  R  V  T  L  G  T  G  R  Q  L         (169)
          *  *  ** *     *        ***    *  * hgt4  GTCATCCTCCAGGTCCAGAGCTATGCCCACTGGCAGGACATCACC           551'
A     TCAGTGCTGGAGGTGCGCGCCTACAAGCGCTGGCAGGACGTGTCC           552
                                         *  *  * hgt4   V  I  L  Q  V  Q  S  Y  A  H  W  Q  D  I  T
A      S  V  L  E  V  R  A  Y  K  R  W  Q  D  V  S         (184)
       *  *      * **     *     *        *  *  ** hgt4  AGGCACCGCATGGAGGTGATCAGCAACTTTTCCCAGCAGCACTTC           596'
A     ATGCGCCGCATGGAGATGATCAGTGACTTCTGCGAGCGGCGCTTC           597
          *  * hgt4   R  H  R  M  E  V  I  S  N  F  S  Q  Q  H  F
A      M  R  R  M  E  M  I  S  D  F  C  E  R  R  F         (199)
       *     ***   *  ***     *     ***** hgt4  CTCGGGGAGGTGGATTACCTTGTGTGTGCAGATGTGGACATGAAG           641'
A     CTCAGCGAGGTGGATTACCTGGTGTGCGTGGACGTGGACATGGAG           642
          *  *  *        *        *     *  *   * hgt4   L  G  E  V  D  Y  L  V  C  A  D  V  D  M  K
A      L  S  E  V  D  Y  L  V  C  V  D  V  D  M  E         (214)
                *  *    *** *   **          *  * hgt4  TTCAACAACCATGTGGGTGTGGAGATCCTCTCTTCCCTGTTTGCC           686'
A     TTCCGCGACCACGTGGGCGTGGAGATCCTGACTCCGCTGTTCGGC           687
          *              *  *  *      * hgt4   F  N  N  H  V  G  V  E  I  L  S  S  L  F  A
A      F  R  D  H  V  G  V  E  I  L  T  P  L  F  G         (229)
          *  **  *  *     **              *  *   **  **
```

```
hgt4  ACCATCCATCCTGGCTTCTATGGGTTCCATCGGGACACCTTTGCC      731'
A     ACCCTGCACCCCGGCTTCTACGGAAGCAGCCGGGAGGCCTTCACC      732
                    *                        *
hgt4    T   I   H   P   G   F   Y   G   F   H   R   D   T   F   A
A       T   L   H   P   G   F   Y   G   S   S   R   E   A   F   T   (244)
       **  **       *       *  ***       *       *  **                *
hgt4  TATGAATGCCAGCCTCAGTCCCAAGCCCATTTTCCTGAGGGTGAA      776'
A     TACGAGCGCCGGCCCCAGTCCCAGGCCTACATCCCCAAGGACGAG      777
           *                *                *
hgt4    Y   E   C   Q   P   Q   S   Q   A   H   F   P   E   G   E
A       Y   E   R   R   P   Q   S   Q   A   Y   I   P   K   D   E   (259)
           **       *  **  **  **           *       *   *       **  **   *
hgt4  GGGGACTTTTATTATATAGGGGCCTTATTTGGTGGGTCAGTGCTG      821'
A     GGCGATTTCTACTACCTGGGGGGGTTCTTCGGGGGGTCGGTGCAA      822
         *       *   *   *                           *   *
hgt4    G   D   F   Y   Y   I   G   A   L   F   G   G   S   V   L
A       G   D   F   Y   Y   L   G   G   F   F   G   G   S   V   Q   (274)
        *   *           *   *  **  **           *   *  **       *
hgt4  GAGGTTTACAGGCTGATCATGGCCTGTCACCAGGTGATGATGATT      866'
A     GAGGTGCAGCGGCTCACCAGGGCCTGCCACCAGGCCATGATGGTC      867
                                    *
hgt4    E   V   Y   R   L   I   M   V   C   H   Q   V   M   M   I
A       E   V   Q   R   L   T   R   A   C   H   Q   A   M   M   V   (289)
       *** *       *   *** **  ***
hgt4  GACCAAGCCAACCACATCGAGGCCCTG<======fy-82======      893'
A     GACCAGGCCAACGGCATCGAGGCCGTGTGGCACGACGAGAGCCAC      912
           *            *   *
hgt4    D   Q   A   N   H   I   E   A   L
A       D   Q   A   N   G   I   E   A   V   W   H   D   E   S   H   (304)

hgt4  ==
A     CTGAACAAGTACCTGCTGCGCCACAAACCCACCAAGGTGCTCTCC      957 hgt4
A       L   N   K   Y   L   L   R   H   K   P   T   K   V   L   S   (319)
```

FIG. 10B

ABO GENOTYPING

CROSS REFERENCE TO RELATED APPLICATION

This application is a continuation-in-part application to Ser. No. 07/402,695, filed Aug. 31, 1989, now U.S. Pat. No. 5,068,191, issued Nov. 26, 1991 which is incorporated herein by reference.

TECHNICAL FIELD

The present invention relates generally to the ABO histo-blood groups. This invention is more particularly related to the genes defining the ABO histo-blood groups, probes to the DNA sequences, methods for identification of histo-blood group ABO status, methods for tumor suppression, DNA constructs, recombinant plasmids, recombinant methods for producing histo-blood glycosyltransferases, purified histo-blood glycosyltransferases and antibodies produced therefrom which bind to protein epitopes.

BACKGROUND OF THE INVENTION

The histo-blood group ABH determinants are major allogeneic antigens in both erythrocytes and tissues of humans. They generally constitute peripheral parts of the oligosaccharide chains of glycoconjugates, i.e., linked to lipids (glycosphingolipids) or to proteins (glycoproteins). The structure of the antigen determinants was established in the 1950s by Watkins and Morgan (*Nature* 180:1038–1040, 1957) and Kabat et al. (*Blood Group Substrates: Their Chemistry and Immuno-chemistry*, 1956, Academics Press, New York). Subsequently, Watkins and Morgan (*Vox Sang.* 4:97–119, 1959) proposed that the A and B phenotypes were associated with glycosyltransferases that converted the H substance associated with O phenotype to A and B, respectively, through the addition of $\alpha 1\rightarrow 3$-N-acetylgalactosamine or $\alpha 1\rightarrow 3$-galactosyl residues to H antigen, Fuc$\alpha 1\rightarrow 2$Gal$\beta 1\rightarrow$R. Thus the primary products of the histo-blood group A and B genes are the respective glycosyltransferases.

At present, knowledge of the histo-blood group antigens is limited to their chemistry, immunology, biosynthesis and genetic inheritance. DNA sequence information for the ABO genes has not been available, due primarily to the difficulty associated with purifying mammalian glycosyltransferases in sufficient quantities. Nucleotide probes based on amino acid sequence information of the A and B transferase proteins would allow cloning and characterization of the ABO genes, and thereby permit methods for direct DNA blood grouping.

Consequently, there exists a need in the art for purified histo-blood group A or B glycosyltransferase and the primary structure of the genes encoding them. The present invention fills this need, and further provides other related advantages.

SUMMARY OF THE INVENTION

Briefly stated, the present invention provides a substantially pure histo-blood group A glycosyltransferase. The protein may be derived from human cells.

Within a related aspect, the present invention discloses antibodies that bind to protein epitopes on histo-blood group A glycosyltransferases. Particularly preferred monoclonal antibodies include WKH-1, produced by a hybridoma designated as ATCC No. HB 10207.

In another aspect of the present invention, an isolated DNA molecule encoding a histo-blood group A glycosyltransferase is disclosed. Within one embodiment, the DNA sequence encodes the amino acid sequence shown in FIG. 3 from alanine, amino acid number 54, to proline, amino acid number 353. In another embodiment, the DNA sequence encodes the amino acid sequence shown in FIG. 3 from methionine, amino acid number 1, to proline, amino acid number 353. Also disclosed is an isolated DNA molecule capable of specifically hybridizing with a DNA molecule encoding a histo-blood group A glycosyltransferase.

Within a related aspect of the present invention, an isolated DNA molecule encoding a histo-blood group B glycosyltransferase and an isolated DNA capable of specifically hybridizing with a DNA molecule encoding a histo-blood group B glycosyltransferase are disclosed. The present invention also discloses both an isolated DNA molecule encoding a protein of a histo-blood group O gene and an isolated DNA molecule capable of specifically hybridizing with a DNA molecule encoding a protein comprising a product of a histo-blood group O gene.

In another aspect of the present invention, methods are provided for detecting histo-blood group ABO status. In one embodiment, the method comprises: isolating DNA from a patient; incubating the DNA with at least three DNA probes under conditions permitting hybridization, wherein one of the probes comprises a nucleotide sequence derived from DNA encoding histo-blood group A glycosyltransferase, or portion thereof, and another of the probes comprises a nucleotide sequence derived from DNA encoding histo-blood group B glycosyltransferase, or portion thereof, and another of the probes comprises a nucleotide sequence derived from DNA of a histo-blood group O gene, or portion thereof; and detecting the presence or absence of a pattern of hybridization of the DNA with the DNA probes, and therefrom determining the histo-blood group ABO status. In another embodiment, the method comprises: isolating DNA from a patient; incubating a first aliquot of the DNA with a DNA probe comprising a nucleotide sequence derived from DNA encoding for histo-blood group A glycosyltransferase, or portion thereof, under conditions permitting hybridization; incubating a second aliquot of the DNA with a DNA probe comprising a nucleotide sequence derived from DNA encoding for histo-blood group B glycosyltransferase, or portion thereof, under conditions permitting hybridization; incubating a third aliquot of the DNA with a DNA probe comprising a nucleotide sequence derived from DNA of a histo-blood group O gene, or portion thereof, under conditions permitting hybridization; and detecting the presence or absence of a pattern of hybridization and therefrom determining the histo-blood group ABO status. In yet another embodiment, the method comprises: isolating DNA from a patient; cleaving the DNA with at least one restriction endonuclease to produce two or more DNA fragments; separating the DNA fragments by size; and detecting the presence of DNA fragments unique to histo-blood group A, or B or O status, and therefrom determining histo-blood group ABO status.

Within a related aspect, DNA constructs comprising a DNA sequence encoding histo-blood group A glycosyltransferase and plasmids comprising the DNA sequence, are disclosed. Suitable promoters and/or polyadenylation signals are also disclosed. In addition, cells transfected with the DNA constructs, and methods for producing histo-blood group A glycosyltransferase using host cells transfected or transformed with a suitable DNA construct are also disclosed. A method for producing A glycosyltransferase comprises: introducing into a host cell an isolated DNA molecule encoding a histo-blood group A glycosyltransferase, or a DNA construct comprising a DNA sequence encoding histo-blood group A glycosyltransferase; growing the host cell in an appropriate medium; and isolating the protein product encoded by the DNA construct produced by the host cell. Similarly, DNA constructs comprising a DNA sequence encoding histo-blood group B glycosyltransferase, plasmids therefrom, and methods for recombinant production of the B glycosyltransferase from an isolated DNA molecule or a DNA construct, are disclosed.

In yet another aspect of the present invention, methods for suppressing tumor growth in a patient are disclosed. The methods generally comprise: establishing a nonpathogenic bacterial cell which contains a DNA sequence encoding histo-blood group A glycosyltransferase; and introducing the bacterial cell into the intestinal tract of a patient, thereby enriching the bacterial flora to A antigen, wherein the enrichment stimulates a humeral immune response to the tumor.

These and other aspects of the present invention will become evident upon reference to the following detailed description and attached drawings.

BRIEF DESCRIPTION OF THE DRAWINGS

FIGS. 1A-1C depict the cloning of A glycosyltransferase.

FIG. 1A depicts a partial amino acid sequence of the internal peptide (K-8) and corresponding degenerate oligodeoxynucleotide sequences used as primers and probes. N-terminal amino acid sequence information (42 a.a.) used for the PCR experiment is shown in bold type. The oligonucleotide sequences of primers FY-1 and FY-2, and probe FY-3, are presented beneath the amino acid sequences of the respective regions. In order to decrease degeneracy, rarely used codons were omitted from the synthesis of FY-1 and FY-2. The degeneracy of these three oligos are 576 (FY-1), 144 (FY-2), and 256 (FY-3), respectively.

FIG. 1B represents the results of a PCR presence test. The nucleotide sequence between oligos FY-1 and FY-2 in genomic and cDNA were amplified by the PCR method and analyzed by polyacrylamide gel/electroblot. Radiolabeled FY-3 oligo probe was used for hybridization. The DNAs tested were: (lane 1) genomic DNA from blood type A individual, (2) B individual, (3) O individual, and (4) random-primed MKN45 cDNA. The positions of marker fragments from phi X 174/Hae III (118 bp and 72 bp) are indicated by arrows.

FIG. 1C represents the results of PCR identification. DNAs from 6 phage candidates (lanes 5-10) were analyzed for the presence of the nucleotide sequence between oligos FY-1 and FY-2 as per the presence test. In lane 11, the 98 bp fragment from the presence test of MKN45 cDNA was gel-purified and used as a control size marker.

FIG. 3A-3C depicts the amino acid sequence of human A transferase inferred from the nucleotide sequence of cDNA clone FY-59-5. Alaninc at a.a. 54 of the N-terminal portion of the soluble enzyme, and a possible N-glycosylation site (Asn at a.a. 112) are indicated in bold type. The positions and the names of the peptide fragments which were sequenced are shown by broken lines (e.g., <K-1>). The mismatches between the deduced and sequenced amino acids are indicated by bold type. The small letters represent ambiguous amino acids and the symbol xxx represents undetermined amino acids. The apparent transmembrane domain is also indicated.

FIG. 5A-5C depicts deduced amino acid sequences from ABO allelic cDNAs. Asterisks indicate residues identical to FY-59-A. Question marks indicate the unidentified sequence due to the absence of a corresponding nucleotide sequence in cDNAs. The symbol (—) denotes the stop codon.

FIG. 6A represents the results of genotyping by diagnostic restriction enzyme digestion.

FIG. 6A depicts allele-specific restriction sites for the ABO allelic cDNAs. Sequences were aligned and numbered to correspond to the FY-59-5 clone coding sequence.

FIGS. 6B and 6C represent the results of diagnostic enzyme digestion analysis of PCR-amplified DNA. Positions of diagnostic fragments are indicated by arrows: b, lanes 1-5, NarI (205 and 262 bp); lanes 6-10, Bss HII (203 and 264); c, lanes 1-5, Alu I (189 and 280); lanes 6-10, HpaII (186). Genomic DNAs were: MKN45 (lanes 1 and 6), SW948 (2 and 7), SW48 (3 and 8), CO-LO205 (4 and 9) and SW1417 (5 and 10).

FIG. 6D represents the results of Southern hybridization detection of the O allele single base deletion. Genomic DNAs were digested with BstEII (lanes 1-5) or KpnI (lanes 6-10) and were the same as (b) and (c). The probe was insert FY-59-5.

FIG. 7 represents a comparison of deduced amino acid sequences for $A^1$ vs. $A^2$ transferases. The initiation codon of membrane-bound forms of $A^1$ transferase is numbered 1 for deduced a.a. sequence. Soluble forms of enzymes start at alanine at a.a. 54. The a.a. at position 156 (marked in bold type) may not be conserved. *, identical a.a. as shown above. =, termination codon. ?, unidentified a.a.

FIG. 8 represents a comparison of nucleotide and deduced amino acid sequences around the area of difference for $A^1$ vs. $A^2$ alleles. The initiation codon and its A residue of membrane-bound forms of $A^1$ transferase are numbered 1 for deduced a.a. and nucleotide sequences, respectively. The symbol (—) indicates the position of single base deletion (one of the Cs from 1059-1061).

FIG. 9 depicts the strategy for PCR cloning of homologous genes. A pair of synthetic oligodeoxynucleotides, fy-81 and 82, were used for PCR amplification of the in-between fragment. Artificial Eco RI site was added to the 5' end of the primers to facilitate cloning procedures. The abbreviations "bGal" "mGal" and "hGal" represent bovine, murine and human α1→3 galactosyltransferases, respectively, and "A" represents histo-blood group A transferase. Numbering for "A" is based on sequencing data for A transferase provided herein, and for "bGal," "mGal" and "hGal", references pertaining to α1→3 galactosyltransferases (Joziasse et al., *J. Biol. Chem.* 264:14290-14297, 1989; Larsen et al., *Proc. Natl. Acad. Sci. USA* 86:8227-8231, 1989; and Larsen et al., *J. Biol. Chem.* 265:7055-7061, 1990).

FIG. 10A-10B depicts a comparison of nucleotide and deduced amino acid sequences of histo-blood group A transferase ("A") and homologous sequence hgt4. The symbols - and / indicate deletion and frameshift position, respectively. In order to obtain maximum homology (among A, hgt4, bGal, mGal and hGal), codon frame was adjusted in the figure. Positions of corresponding regions for oligos are also indicated. The symbol * indicates conserved nucleotides and amino acids among these genes.

DETAILED DESCRIPTION OF THE INVENTION

Figure 2:
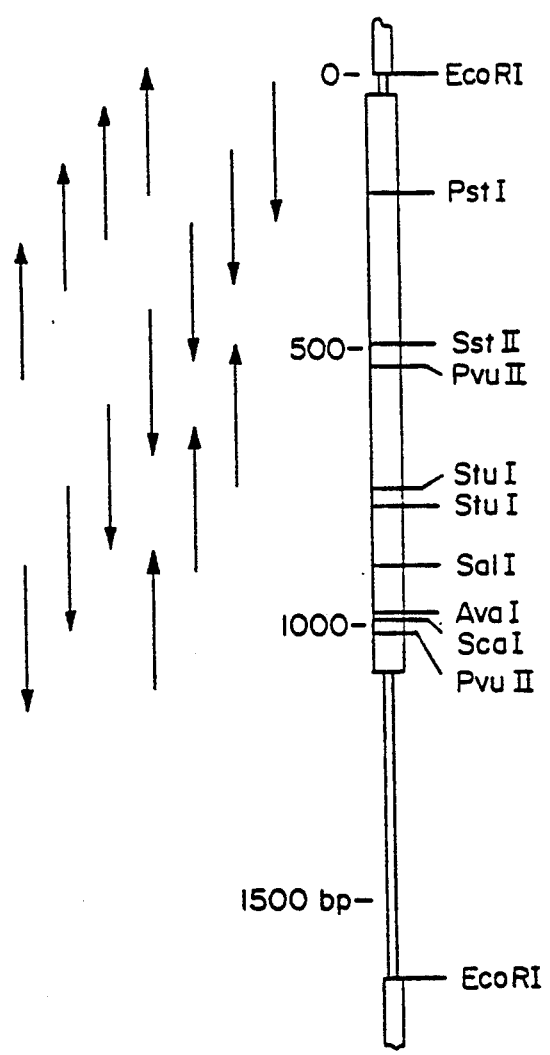
FIG. 2 illustrates the restriction map for cDNA clone (FY-59-5) encoding human A transferase, and the sequencing strategy. The protein coding region is represented by the dotted box and the non-coding regions by the closed bar. The arrows beneath the cDNA indicate direction and extent of sequencing.

Prior to setting forth the invention, it may be helpful to an understanding thereof to set forth definitions of certain terms to be used herein.

Antibody—as used herein, includes an intact molecule, a fragment thereof, or a functional equivalent thereof; and may be genetically engineered. Examples of antibody fragments include F(ab')$_2$, Fab', Fab and Fv Complementary DNA or cDNA—a DNA molecule or sequence which has been enzymatically synthesized from the sequences present in an mRNA template, or a clone of such a molecule.

DNA Construct—a DNA molecule, or a clone of such a molecule, either single- or double-stranded, which has been modified to contain segments of DNA which are combined and juxtaposed in a manner which would not otherwise exist in nature.

Plasmid or Vector—a DNA construct containing genetic information which may provide for its replication when inserted into a host cell. A plasmid generally contains at least one gene sequence to be expressed in the host cell, as well as sequences which facilitate such gene expression, including promoters and transcription initiation sites. It may be a linear or closed circular molecule.

The present invention provides the histo-blood group A glycosyltransferase. This protein, also known as UDP-GalNAc:Fucα1→2Galα1→3GalNAc transferase, catalyzes the transfer of α1→3GalNAc to substrates such as Fucα1→2Galβ1→R (H antigen).

Histo-blood group A glycosyltransferase may be isolated by a combination of extraction and chromatography techniques. Briefly, in one embodiment, enzyme activity is extracted from mammalian cells by homogenization and solubilization with detergent. The detergent extract is passed over a gel filtration column. Fractions containing enzyme activity are further purified by cation exchange chromatography. Final purification is performed using reverse-phase column chromatography.

A variety of body fluids and tissues, such as plasma, kidney and lung, are suitable for purification of histo-blood group A transferase. A preferred source of starting material for such purification is human cells. A representative isolation procedure is as follows. Homogenization of tissue in a buffer solution containing a detergent such as Triton X-100 yields a solution with constant A transferase activity. The soluble supernatant of the extract may be adsorbed on Sepharose 4B and eluted with UDP. The ability of Sepharose 4B to adsorb A transferase, and elution of the enzymatic activity, appear to be lot-dependent. The selectivity of the binding to Sepharose may be shown by the specific elution with UDP and not GDP, UMP or 0.2M NaCl. Further purification of the enzyme is accomplished by cation exchange chromatography, e.g., by application of a diluted and pH-adjusted Sepharose 4B eluate to a mono-S HR 5/5 column. Where it is desired to combine and concentrate single enzyme preparations, a second cation exchange chromatography step may be utilized. Final purification of the histo-blood group A transferase to homogeneity is achieved by reverse phase chromatography, e.g., by application of a diluted and pH-adjusted cation exchange eluate to a proRPC H5/10 column.

A representative purified histo-blood group A transferase of the present invention has the following characteristics. Sodium dodecyl sulfate polyacrylamide gel electrophoresis (SDS-PAGE) shows a single protein band with apparent molecular weight (MW) of approximately 40,000 under both reducing and nonreducing conditions. The 40,000 MW band is the only band to increase with the increases in specific activity associated with the steps in the purification process, and the band is absent in extracts of tissue from O individuals. Digestion with N-glycanase results in a reduction in MW of about 6,000 (as estimated by SDS-PAGE), indicating that the A transferase is a glycoprotein with at least one N-linked carbohydrate chain. The amino acid composition and partial amino acid sequence was determined for the purified A transferase.

The present invention also provides antibodies that bind to histo-blood group A transferase. The antibodies are useful tools for the cytolocalization, e.g., by immuno-gold electron microscopy, of glycosyl-transferases and for elucidating their role in cellular differentiation and malignant transformation. The purified native histo-blood group A transferase protein described above may be utilized to produce polyclonal or monoclonal antibodies which bind to the A transferase protein. It will be evident to one skilled in the art that antibodies to fragments of A transferase or to intact, denatured A transferase may also be produced. The latter type of antibodies are particularly useful for detection of "fixed, " e.g , . formaldehyde or glutaraldehyde, cells expressing A transferase.

Briefly, polyclonal antibodies may be produced by immunization of an animal and subsequent collection of its sera. It is generally preferred to follow the initial immunization with one or more boosters prior to sera collection.

Monoclonal antibodies (MAbs) may be generally produced by the method of Kohler and Milsrein (*Nature* 256:495-497, 1975; *Eur. J, Immunol.* 6:511-519, 1976). Briefly, the lymph nodes and/or spleens of an animal injected with purified protein are fused with myeloma cells to form hybrid cell lines ("hybridomas" or "clones"). Each hybridoma secretes a single type of immunoglobulin specific for the protein, and, like the myeloma cells, has the potential for indefinite cell division.

The MAbs of the present invention are produced by immunization of an animal with substantially pure histo-blood group A transferase. Spleen cells are fused with myeloma cells and hybridomas cloned by limiting dilution procedures. Hybridomas may be selected on the basis of reactivity with the purified native A transferase protein which is attached to a solid phase, staining of blood group A cells possessing high A transferase activity, and immunoprecipitation of transferase activity. This strategy for screening hybridomas allows for the selection of "functional" antibodies, i.e., ones capable of immunoprecipitating and inhibiting transferase activity. Am additional screening for the absence of reactivity with blood group ABH carbohydrate determinants permits the selection of hybridomas secreting MAbs directed to protein epitopes associated with the A transferase, but not its immunodominant ABH carbohydrate determinants.

A representative MAb, WKH-1, is produced by a hybridoma designated by ATCC No. HB 10207. The MAb reacts with cells having high A transferase activity and immunoprecipitates the A transferase activity as well as iodinated 40,000 MW iodinated transferase protein. The MAb immunoprecipitates and partially inhibits not only $A_1$ and $A_2$, but also B transferase activity, and reacts with B cells expressing B transferase, thus indicating a cross-reactivity with B transferase. In contrast, the MAb has shown no reactivity with various cells having the O phenotype. It will be evident to those skilled in the art that other MAbs, including ones that competitively inhibit the formation of an immunocomplex between WKH-1 and histo-blood group A transferase, may be produced.

The present invention also provides isolated DNA molecules, including genomic DNA and cDNA, encoding histo-blood group A transferase. Based on the partial amino acid sequence of the purified A transferase, the cDNA encoding this protein was cloned. The cloning strategy may be briefly summarized as follows: 1) synthesis of degenerate oligodeoxynucleotides reverse translated from amino acid sequence; 2) cDNA preparation; 3) polymerase chain reaction (PCR) presence test; 4) preparation of amplified fragment; 5) cDNA library construction; 6) PCR presence test for amplified cDNA library (optional); 7) screening the library with amplified fragment probe; and 8) PCR identification test. More specifically, for the isolation of a representative DNA molecule encoding a histo-blood group A glycosyltransferase, poly A+RNA from the human stomach cancer cell line MKN45 (which expresses high levels of A-antigen) was used for construction of a λgt10 cDNA library. Alternatively, a cDNA library has been constructed from human tissues. Degenerate synthetic oligodeoxynucleotides were used for polymerase chain reactions to detect the presence of the sequence of interest in cDNA (presence test), and to identify the correct clones (identification test) after screening the library with a radiolabeled PCR amplified fragment.

Oligonucleotide probes based on the partial amino acid sequences of A transferase protein were constructed as shown in FIG. 1A. cDNA was constructed by random-priming, and PCR analysis was used to ascertain whether the sequence of interest was present in the cDNA (presence test). As shown in FIG. 1B, a 98 bp fragment of the expected size was obtained, as detected by FY-3 oligomer probe for the internal sequence of the amplified fragment. Subsequently, this fragment was gel-purified and used to screen the cDNA library after $^{32}$P-labeling in a PCR reaction. Stringent hybridization and washing conditions were employed (e.g., Suggs et al. in *Developmental Biology Using Purified Genes*, eds. D. Brown and C. F. Fox, p. 683, Academic Press, N.Y., 1981). Identity of the candidate clones was tested by PCR (identification test). Three out of 10 clones had a 98 bp sequence in the cDNA insert (FIG. 1C). After subcloning into the pT7T3 plasmid, this insert was used as a radioactive probe for rescreening the same library, and 15 clones were isolated from the library of one million independent clones with cDNA inserts.

The cDNA clones obtained contained variable internal sequences, in addition to the variable 5' and 3' ends. The clones were grouped by the presence of certain sequences, which were identified as introns based on the presence of termination signals in the coding frame. These clones may be derived from the unspliced or partially spliced mRNA. A repetitive sequence was found downstream of the coding region.

Eco RI cDNA inserts were subcloned into the Eco RI site of pT7T3 plasmid or Phagescript SK for detailed analysis. The restriction map of one of the clones, FY-59-5, is shown in FIG. 2. Several other clones show variable mapping due to the presence of intron sequences in addition to variable 5'- and 3'- ends. Several deletion constructs were prepared for sequencing. Sequencing was performed for both strands for the entire coding sequence (FIG. 2).

cDNA clone FY-59-5 has a long coding sequence of 1062 bp (FIG. 3), which encodes a protein of MW 41,000. The first methionine codon appears to be the initiation codon. The amino acid composition of the soluble form of A transferase is in close agreement with the one deduced from the corresponding nucleotide sequence. As discussed above, the MW of N-glycanase-treated A transferase was found to be 34,000, which is in agreement with the value deduced from the nucleotide sequence. All peptides sequenced from the purified A transferase were accounted for, and were nearly identical to the predicted amino acid sequences. Thus, the obtained cDNA clone encodes the 41,000 MW protein which was described above as the histo-blood group A transferase.

The N-terminus of the soluble form of purified A transferase begins with the alanine at position 54. A hydrophobic region spanning 21 amino acids precedes this N-terminus and appears to be the transmembrane region of the membrane-bound form of A transferase. A proline-rich region (9 out of 60) follows the hydrophobic region. An N-glycosylation site appears to be located at position 112 (N-T-T). The remaining long C-terminal portion is moderately hydrophilic.

Based upon hydrophobicity plot analysis, the A transferase consists of three domains: a short N-terminal, a hydrophobic transmembrane, and a long C-terminal domain. Since the purified soluble form of this enzyme is catalytically active but lacks the N-terminal and hydrophobic domains, the long C-terminal domain appears to contain the catalytic domain.

Southern hybridization was performed to analyze for restriction fragment length polymorphisms (RFLP) among DNAs from sources with differing ABO blood group antigens. In order to detect the A transferase mRNA, Northern hybridization experiments were performed. Multiple bands were detected in RNAs from cell lines of A, B, AB, and even O phenotype. Thus, the sequences of ABO genes appear to be essentially very similar.

The present invention also provides isolated DNA molecules, including genomic DNA and cDNA, encoding histo-blood group B glycosyltransferase and encoding a protein product, if any, of a histo-blood group O gene. Histo-blood group B glycosyltransferase, also known as UDP-Gal:Fucα1→2Galα1→3Gal transferase, catalyzes the transfer of α1→3 Gal to substrates such as Fucα1→2Galβ1→R (H antigen). No similar transferase activity is associated with the O phenotype. Using an A transferase cDNA probe, B allelic cDNA clones (e.g., from the human colon adenocarcinoma cell line, SW 1417, available from ATCC), and O allelic cDNA clones (e.g., from the human colon adenocarcinoma cell line, Colo 205, available from ATCC) were prepared. A summary of these clones and others provided by the present invention is shown in Table 1.

TABLE 1

| | | Classification of cDNA clones[1] | | |
|---|---|---|---|---|
| Source of RNA | Pheno- type | Blood type | cDNA clones | Genotype |
| MKN-45 | A | ND | 59-5, 59-7 | A |
| SW948 | O | O | 65-1, 65-10, 65-15, 65-18 | O |
| SW48 | AB | AB | 66-1, 66-2, 66-3, 66-7 66-9 | A B |
| COLO-205 | O | ND | 68-6, 68-11, 68-12, 68-14, 68-15 | O |
| SW1417 | B | B | 69-2, 69-7 69-3, 69-4, 69-8 | O B |

[1]Each cDNA clone was classified by the library. Allelic cDNAs were separated based on nucleotide sequence. Phenotype of the cell line, blood type of host, and genotype are indicated.
ND, not determined.

As shown in Table 1, the two clones FY-59-5 and FY-59-7 (from the MKN45 cDNA library) were identified as representing A-gene alleles. These clones showed identical sequences for corresponding regions, and the deduced amino acid sequences of these clones matched that of purified A transferase. However, they showed different 5' and 3' ends, as well as different splicing patterns. Four cDNA clones (FY-65-1, FY-65-10, FY-65-15, FY-65-18) obtained from the cDNA library of SW948 (phenotype O, genotype OO) showed identical nucleotide sequences, and were judged as representing an O gene allele. cDNA clones from SW48, the AB cell line, were divided into two groups: clones FY-66-1, FY-66-2, FY-66-3, FY-66-7 belong to the same group, whereas clone FY-66-9 differs by several base substitutions, resulting in four amino acid substitutions. On the basis of nucleotide sequence similarities between FY-66-1, FY-59-5, and FY-59-7, the group represented by FY-66-1 appears to be the A allele and the other represented by FY-66-9 appears to be the B allele at the ABO locus.

Figure 4:
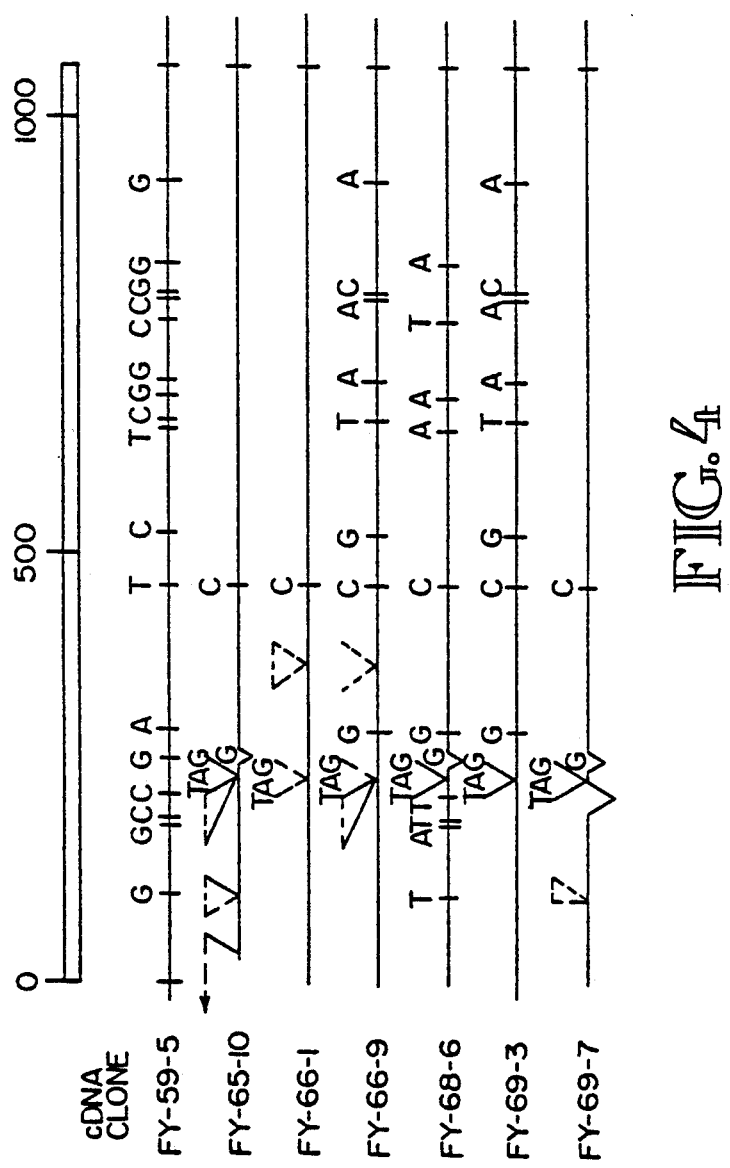
FIG. 4 depicts a comparison of nucleotide sequences of clones for five cell lines of different ABO status (Table 1). FY-59-5 (a representative A allelic cDNA clone whose sequence is depicted in FIG. 3) is compared with representative cDNA clones from various cell origins. Insertions are shown above the line and deletions below the line. The nucleotide sequences in various clones are identical to FY-59-5, except those indicated above the line.

The nucleotide sequences of clones from five cell lines of different ABO status were compared (FIG. 4). Based on this comparison, seven single base substitutions between A and B clones are identified (nucleotide positions 294, 523, 654, 700, 793, 800 and 927). Four consistent nucleotide substitutions lead to amino acid changes (residues 176, 235, 266 and 268) between A and B allelic cDNAs (FIG. 5). The disclosure of the present invention also shows that the third and fourth amino acid substitutions (a.a. 266 and 268) are crucial in determining sugar-nucleotide specificity, and the second a.a. substitution (a.a. 235) also affects specificity. The cDNA clones representing an O gene allele are identical to the A allele except for a single base deletion (G at nucleotide position 258). This deletion, located close to the amino terminus, results in a shift of the reading frame (FIG. 5) and presumably leads to translation of an enzymatically inactive protein. Thus, the lack of transferase activity in O individuals is due to a shift in the reading frame.

Because polymorphism of ABO phenotypes is known to exist, e.g., the A1–A2 subgroup, it will be evident to one skilled in the art that variants in the ABO genes occur. Variants may be isolated by the procedures described herein for representative ABO genes and may be identified based upon the type of antigen expressed by the cell, the specific enzymatic activity detected, and/or other methodology such as that involving hybridization. Alternatively, the molecular basis for a particular subtype may be elucidated by PCR amplification of genomic and cDNA of individuals of that subtype and subsequent direct sequencing of the amplified fragments. The term "isolated DNA molecule" as used herein includes both the representative ABO genes described above and variants of these genes. DNA molecules may also be isolated which do not encode the protein products of the A, B, and O genes, but which are capable of specifically hybridizing with a DNA molecule encoding the A, B, and O gene products, respectively.

Based upon the ABO sequence information and material described above, nucleotide probes may be produced, e.g., by PCR amplification, and used for DNA or RNA diagnostic procedures (Landegren et al., Science 242:229, 1988) involving the histo-blood group glycosyltransferases. As disclosed within the present invention, differences in the sequences of A, B, and O genes permit preparation of probes selective for these genes. It will be evident to one skilled in the art that the probes may comprise a nucleotide sequence derived from DNA encoding the gene product, or a portion of such DNA. Oligodeoxynucleotides may be synthesized (Tan et al., Cold Spring Harbor Symp. Quant, Biol., Vol. 47, p. 383) or prepared with a DNA synthesizer, e.g., an Applied Biosystems DNA Synthesizer 380B.

Procedures of the present invention employing the nucleotide probes, versus antibodies, permit a higher degree of accuracy and increased sensitivity. Applications of such nucleotide probes include blood group ABO typing, which is useful for blood transfusions, organ transplantations and forensic medicine. In forensic applications, samples that have been stored for years, e.g., a piece of hair, a spot of body fluid or blood, or tissue sections, could by utilized for identification of the histo-blood group.

Suitable methods for determining histo-blood group ABO status by use of nucleotide probes include DNA hybridization. For example, to detect histo-blood group ABO status, at least three DNA probes are prepared. In one embodiment, one of the probes ("A probe") comprises a nucleotide sequence derived from DNA encoding histo-blood A glycotransferase, another probe ("B probe") comprises a nucleotide sequence derived from DNA encoding histo-blood group B transferase, and another probe ("O probe") comprises a nucleotide sequence derived from DNA of a histo-blood group O gene. DNA from a patient is isolated. The hybridization of the probes with DNA isolated from a patient may be performed with all the probes present or with each probe incubated with separate aliquots of the patient's DNA.

For example, in one embodiment, a single aliquot of the patient's DNA is incubated with the three DNA probes described above (A, B and O probes) under conditions permitting hybridization. If hybridization has occurred, a pattern of hybridization is detected which is diagnostic for the presence of histo-blood group A status, B status or O status. The step of detecting may be performed by use of a reporter group, bound to the probe, to a molecule that reacts with the probe, or to a second molecule that reacts with the first molecule. Suitable reporter groups include radioisotopes, fluorophores, enzymes, luminescers, and dye particles. Each DNA probe may contain a different reporter group.

In another embodiment for determining histo-blood group ABO status by DNA hybridization, the probes described above (A, B and O probes) are incubated separately with different aliquots of a patient's DNA. For example, a first aliquot of the DNA is incubated with the A probe, a second aliquot is incubated with the B probe, and a third aliquot of the DNA is incubated with the O probe. A pattern of hybridization of the first aliquot is diagnostic for the presence of histo-blood group A status, a pattern of hybridization of the second aliquot is diagnostic for the presence of B status, and a pattern of hybridization of the third aliquot is diagnostic for the presence of O status. The discussion above regarding the step of detecting is applicable here as well.

It may be desirable for either method involving hybridization to cleave the DNA isolated from a patient to produce DNA fragments. Such cleavage may be performed by digestion of the DNA with at least one restriction endonuclease. In addition, it may be desirable for either method involving hybridization to amplify the DNA isolated from a patient. Such amplification may be performed using PCR methodology. Oligodeoxynucleotide hybridization methodology and application of PCR are well known in the art (e.g., Miyada et al., *Methods in Enzymology*, Vol. 154, p. 94; Bos et al., *Nature* 327:293, 1987).

Another suitable method for determining histo-blood group ABO status involves distinguishing DNA fragments by size. For example, DNA is isolated from a patient and cleaved with at least one restriction endonuclease to produce two or more DNA fragments. The fragments are separated by size and histo-blood group ABO status is determined from the detection of the presence of DNA fragments unique to histo-blood group A, or B or O status. For example, allele-specific restriction sites include Nar I and Alu I. These restriction enzymes when combined with PCR yield allele-unique fragments.

Another aspect of the present invention based upon the cloning and characterization of the A and B transferase genes is the preparation of DNA constructs and recombinant plasmids. As noted above, the term "DNA constructs" as used herein comprises segments of DNA which are combined and juxtaposed in a manner which would not otherwise exist in nature. More specifically, DNA constructs may comprise a DNA sequence encoding histo-blood group A, or B, glycosyltransferase in which there has been one or more deletions, substitutions, additions, and/or insertions, relative to "isolated" DNA sequences. A portion of the DNA sequence may be derived from a genomic or cDNA clone. The DNA described herein may include a suitable promoter.

Examples of DNA constructs which may be created include chimeras, such as A-B chimeras with both A and B transferase activities. Briefly, as noted above, there are four amino acid substitutions (a.a. 176, 235, 266 and 268) in the coding region of A and B alleles. These are arginine, glycine, leucine, and glycine in A allele and glycine, serine, methionine, and alanine in B allele. These substitutions sites are all located in Sst II-Ava I fragment. Also in this fragment are single restriction enzyme digestion sites for Bst YI, Fok I, and Mbo II which separate these four substitutions. Therefore, these sites may be used for constructions. In order to omit the influence of differences of 5' and 3' untranslated region, Sst II-Ava I vector fragment of p59-5/66-7(s) can be used to accommodate the Sst II-Ava I chimeric constructs. After constructs are made, Sst II-Bam HI (in pSG-5 vector, e.g., from Stratagens, La Jolla, Calif.) fragment may be transferred into p66-1(s) replacing Sst II-Bam HI fragment.

One embodiment of a method for producing histo-blood group A, or B, glycosyltransferase comprises introducing into a host cell an isolated DNA molecule encoding a histo-blood group A, or B, glycosyltransferase, or a DNA construct comprising a DNA sequence encoding histo-blood group A, or B, glycosyltransferase. The host cells are grown in an appropriate medium and the protein product encoded by the isolated DNA molecule or the DNA construct produced by the host cell is isolated. Preferred host cells include mammalian cells. Particularly preferred host cells include HeLa cells and COS-1 cells. Suitable methods for introducing cloned DNA sequences into cultured mammalian cells include calcium phosphate mediated transfection (e.g., Wiglet et al., *Cell* 14:725, 1978; Corsaro and Pearson, *Somatic Cell Genetics* 7:603, 1981; Graham and Van der Eb, *Virology* 52:456, 1973). It will be evident to one skilled in the art that it is not necessary to use the entire sequence when producing recombinant A or B transferase proteins.

Within a preferred embodiment of the present invention, recombinant plasmids capable of expressing glycosyltransferase comprise a promoter followed downstream by a DNA sequence encoding histo-blood group A, or B, transferase, which in turn is followed downstream by a polyadenylation signal. The DNA sequence may be cDNA or genomic DNA. The plasmids may be used to transiently or stably transfect (transform) cells and thereby establish a cell line which expresses glycosyltransferase (*Current Protocols in Molecular Biology*, Vol. 1 & 2, Wiley Interscience).

Another aspect of the present invention provides a method for suppressing tumor growth in a patient comprising establishing a nonpathogenic bacterial cell which contains a DNA sequence encoding histo-blood group A glycosyltransferase. The bacterial cell is then introduced into a patient, thereby enriching the bacterial flora to A antigen. This enrichment stimulates a humoral immune response to the patient's tumor. Suitable nonpathogenic bacteria include strains of Lactobacillus. A bacterial cell expressing A antigen may be established by introducing a DNA sequence encoding histo-blood group A glycosyltransferase into the bacterial cell.

The following examples are offered by way of illustration and not by way of limitation.

EXAMPLES

Example 1

Purification of Human UDP-GalNAc: Fucα1→Gal α1→3-N-acetylgalactosaminyltransferase

A. Determination of α-GalNAc Transferase Activity (1) Glycolipids. The α-GalNAc transferase activity was determined in reaction mixtures containing 10 mM Tris buffer (pH 7.4), 25 μg $H_1$ or $H_2$ type 2 chain substrate glycolipid, 2 μmol $MnCl_2$, 0.5 μmol CDP-choline, 40 μg Cutscum, 11 nmol UDP[$^{14}$C]-GalNAc (22,816 cpm/nmole; labeled from Amersham and unlabeled from Sigma Chemical Co.), and enzyme preparations as described below, in a total volume of 100 μl. Radioactive glycolipid products were located by autoradiography, scraped from the plate, and counted using a liquid scintillation counter. Identification of the reaction product was assessed by high-performance thin-layer chromatography (HPTLC) immunostaining using Anti-A MAbs with well-characterized specificity, as previously described by Clausen et al. (*J. Immunol.* 136:326-330, 1986).

(2) 2-Fucosyllactose. Transferase activity was determined in the same reaction mixture as for glycolipid assay, but with omission of Cutscum and a lower specific activity of sugar nucleotide (4,000 cpm/nmole). The acceptor substrate 2-fucosyllactose (2'FL) was used in concentrations of 5-10 mM, and product determined by scintillation counting after Dowex-1 formic acid cycle chromatography.

B. Isolation to Homogeneity

Buffers: pH measured at room temperature. Buffer A: 100 mM NaCl, 50 mM cacodylic acid, 2 mM $MnCl_2$, 1 mM ethylenediaminetetraacetic acid (EDTA), 1% Triton X-100, pH 6.7. Buffer B: 100 mM NaCl, 50 mM cacodylic acid, 20 mM $MnCl_2$, 1 mM EDTA, 0.1% Triton X-100, pH 6.5. Buffer C: 50 mM cacodylic acid, 20 mM $MnCl_2$, 1 mM EDTA, 50 μM UDP, 0.1% Triton X-100, pH 7.5. Buffer D: 50 mM cacodylic acid, 2 mM $MnCl_2$, 1 mM EDTA, pH 6.5.

Several human enzyme sources were tested, and lung tissue chosen on the basis of apparent high specific activity and the fact that this enzyme activity apparently was mostly soluble. Blood group A and AB lungs (no information on A subgroup status was available) frozen (−80° C.) 24-72 hrs post mortem were used. During purification, glass tubes siliconized by 1% pro-sil-28 (Thomas Scientific) followed by 30 min heating (100° C.) were used. All steps of purification were performed at 4° C.

Step 1.: Extraction and purification procedures up to step 4 were carried out with one single lung (1-2 kg) at a time. Thawed tissues were homogenized in 2×vol of buffer A in a one-gallon Waring blender (four 10-20 sec homogenization with 30 sec interval). The crude homogenate was centrifuged for 1 hr at 10,000 rpm in a Beckman JA-10 rotor. The supernatants were further filtered through Whatman No. 1 paper.

Step 2: Sepharose 4B chromatography: Batches of 4 l of supernatant extract were passed over pre-equilibrated 40 ml Sepharose 4B (lot #56F0333 & 56F0377, purchased from Sigma) columns of diameter 30 mm (Biorad) at a flow rate of ≈3 ml/min. The column was washed with 200 ml buffer B and eluted with 100 ml of buffer C, containing 50 μM GDP or UMP as well as 0.2M NaCl did not elute the enzyme activity, but removed other contaminating proteins. The increased washing effect, however, reduced the yield at elution. Fractions containing enzyme activity (≈30 ml) were pooled, diluted with 50 mM cacodylate buffer (pH 6.0) to a final volume of 50 ml, and adjusted to pH 6.2 with 1M free cacodylic acid. The enzyme with addition of 25% glycerol was stable on ice for several days without significant loss of activity, and could be kept at −30° C. for months without loss of activity.

Step 3: Primary cation exchange (Mono-S HR 5/5) chromatography: The diluted and pH-adjusted Sepharose 4B eluate was applied to a mono-S HR 5/5 column through a 50 ml superloop in conjunction with a Pharmacia (Upsala, Sweden) fast pressure liquid chromatography (FPLC) system. The column was equilibrated in buffer D and washed with 20 ml of the same. Elution was obtained by a gradient of 0-0.5M NaCl in buffer D in 23 ml with a flow rate of 1 ml/min. Fractions containing enzyme activity (≈5 ml) were pooled and 25% glycerol added. At this stage, the enzyme without glycerol was very unstable, but with glycerol it was stable for 24-48 hrs on ice and for weeks at −30° C.

Step 4: Secondary ion exchange (mono-S HR 5/5) chromatography: Pooled fractions from 6-8 individual lung extracts kept frozen after the primary mono-S HR 5/5 column step (step 3) were pooled and diluted with buffer D to 100 ml and reapplied through 2 volumes of a 50 ml superloop to the mono-S column. The chromatography was as described for step 3. This step allowed concentration and removal of glycerol, in addition to some purification as evidenced by the UV (280 nm) elution profile.

Step 5: Reverse phase (proRPC H5/10) chromatography: In order to obtain homogeneous protein free of salt and buffer without significant loss, the eluate (≈5 ml) of secondary mono-S chromatography (step 4) were diluted with 0.1% trifluoroacetic acid (TFA) to a final volume of 10 ml and pH adjusted with TFA to 2.5. The sample was applied in a 10 ml superloop to a proRPC H5/10 column in conjunction with a Pharmacia FPLC system. This column was washed with 10 ml 0.1% TFA and eluted with a gradient of 0-80% acetonitrile in 0.1% TF in 40 ml at a flow rate of 0.3 ml/min. Fractions were pooled based on UV (280 nm) absorption and sodium dodecyl sulfate polyacrylamide gel electrophoresis (SDS-PAGE) profile.

EXAMPLE 2

Determination of Amino Acid Composition and N-terminal Sequence

An enzyme preparation taken through step 5 of Example 1 from a total of 6-8 lungs (equivalent of 10-12 kg of tissue) was used. Fractions containing the homogeneous A transferase protein were pooled and lyophilized in a Speed Vac concentrator in siliconized plastic microfuge tubes. Protein was hydrolyzed at 110° C. for 24 hours or 74 hrs in 6N HCl under vacuum and applied to an amino acid analyzer (Hitachi L-8500).

TABLE 2

| Amino Acid Compositions (moles/mole enzyme)[a] | | | |
|---|---|---|---|
| | 24 hr hydrolysis | 72 hr hydrolysis | mean value[b] |
| Asp/Asn | 22.41 | 22.44 | 22.43 |
| Thr | 16.25 | (15.57) | 16.25 |
| Ser | 16.25 | (13.26) | 14.96 |
| Glu/Gln | 38.18 | 37.91 | 38.05 |
| Gly | 21.25 | 21.18 | 21.22 |

TABLE 2-continued
Amino Acid Compositions (moles/mole enzyme)[a]

|  | 24 hr hydrolysis | 72 hr hydrolysis | mean value[b] |
|---|---|---|---|
| Ala | 17.78 | 17.78 | 17.78 |
| Val | 31.93 | 30.94 | 31.44 |
| Cys/2 | 0.75 | (0.10) | 0.75 |
| Met | 3.37 | (2.89) | 3.37 |
| Ile | 9.79 | 9.32 | 9.56 |
| Leu | 30.60 | 29.92 | 30.26 |
| Tyr | 13.43 | 12.58 | 13.01 |
| Phe | 16.18 | 16.39 | 16.29 |
| Lys | 13.74 | 13.91 | 13.83 |
| His | 10.54 | 10.91 | 10.73 |
| Arg | 21.96 | 22.00 | 21.98 |
| Pro | 16.25 | 18.67 | 17.46 |
| Trp | ND | ND | ND |
| Total |  |  | 299.37 |

[a]Amino acid composition is expressed as moles of residue per mole of A transferase (estimated MW 34,000, excluding carbohydrate moiety).
[b]Unstable amino acids such as Thr, Ser, Cys, and Met were taken from the 24 hr hydrolysis values.

Apparently, 30 μg of the A transferase was carboxymethylated after reduction, and further purified by TSK G2000SW column. The N-terminal sequence of this component was determined by automated Edman degradation using a sequencer. The A transferase was also degraded by Achromobacter endolysyl peptidase, the peptide released was fractioned on high-pressure liquid chromatography (HPLC) through TSK G2000SW sXL column, and various peptides (K1 through K9) were separated. Each peptide was sequenced as described above.

TABLE 3
Amino Acid Sequence of N-terminal Region and Various Peptides Released by Achromobacter Endolysyl Peptidase and by Cyanogen Bromide Cleavage from the A Transferase[1]

N-terminal sequence from intact A enzyme
AVREPDHLQRVSLPRMVYPQXKVL
(Sequence ID No. 1)
Peptides released by Achromobacter endolysyl peptidase

| K1 | VLTPQXK |
|---|---|
|  | (Sequence ID No. 2) |
| K2 | YLLRHKPTK |
|  | (Sequence ID No. 3) |
| K3 | LRFTAVPK |
|  | (Sequence ID No. 4) |
| K4 | AVREPDHLQRVSLPRMVYPQXK |
|  | (Sequence ID No. 5) |
| K5 | DFMVGHRVHYYVFTXXPAAVPRVTL-- |
|  | (Sequence ID No. 5) |
| K7 | VLSPEYLWDQXLLGWPAVLXK |
|  | (Sequence ID No. 7) |
| K8 | dEGhFYYLGGFFGGSVQEVQRLTRAQ/CXQAMMVDQAnGIEAV-- |
|  | (Sequence ID No. 8) |
| K9 | rVLVVT-- |
|  | (Sequence ID No. 9) |

Peptides released by cyanogen bromide degradation

| M4: | VYPQPKVLTPCRKDVLVVTPWLAPIVWEGTFNIDILNeqf-- |
|---|---|
|  | (Sequence ID No. 10) |
| M5: | EFRDHVGVEILTPLFGTLHPgFYXeXXEAF-- |
|  | (Sequence ID No. 11) |
| M6: | VDQANGIEAV-- |
|  | (Sequence ID No. 12) |
| M7: | VGHRVHYYVFTDQPAAVPRVTLGTGRQLSVLEvrAYy-- |
|  | (Sequence ID No. 13) |
| M8: | ISDFCERRFLSEVDVLVCVD-- |
|  | (Sequence ID No. 14) |
| M9: | AVREPDHLQRVSLPRM |
|  | (Sequence ID No. 15) |

Combined N-terminal sequence

|----intact enzyme-----|
|---------K4----------|--K1--|------------K9--------------→
AVREPDHLQRVSLPRMVYPQPKVLTPCRKDVLVVTPWLAPIVWEGTFNIDILNeqf
|------M9------|-----------------M4----------------------→
(Sequence ID No. 16

[1]X, unidentifiable residue; lower case letter, low yield of the amino acid residue having the corresponding upper case designation.

Example 3
Preparation and Characterization of MAbs Directed to Human Histo-Blood Group A Transferase

A. Generation of MAbs

Production of three MAbs, WKH-1, -2, and -3, directed to human blood group A glycosyltransferase, were obtained by immunization of 3-month-old BALB/c mice. Mice were immunized with A transferase (prepared as described in Example 1) emulsified in Ribi's adjuvant (monophosphoryl lipid A+trehalose dimycolate) by intraperitoneal injection 4 times (3 week interval), with approximately 30 μg of transferase per injection. Spleen cells were fused with NS-1 myeloma cells 3 days after the last immunization, and hybridomas were cloned by limiting dilution at least 3 times. Hybridomas were screened by particle-concentrated fluorescence immunoassay (PCFI), fluorescent staining of blood group A cells with high A transferase activity (MKN-45) and immunoprecipitation of transferase activity. Controls included various A glycolipids (prepared as described by Clausen et al., *Biochemistry* 25:7075-7085, 1986) and cell lines with no A or B transferase activity (Colo205). Isotype and subclass were determined by PCFI using goat anti-mouse fluorescein isothiocyanate (FITC)-conjugated antibodies, as well as by the Ochterlony method of using rabbit anti-mouse antibodies (Boehringer Mannheim Biochemicals). MAbs were used as tissue culture supernatants unless otherwise indicated. Antibodies were purified on a protein A Sepharose 4B column (pH 9.0) eluted with 100 mM citrate buffer (pH 4.2), and dialyzed against 20 mM Tris buffer (pH 7.4).

B. PCFI Screening

Approximately 50 µg of purified transferase (prepared as described in Example 1) was mixed with 1 ml of 0.5% (w/v) Fluoricon Carboxyl-Polystyrene Assay Particles (0.86 µm, Pandex) and covalently coupled by adding solid 1-ethyl-3[3-dimethyl-aminopropyl]carbodiimide to give a final concentration of 1 mg/ml. Controls for reactivity with carbohydrates included beads similarly coated with salivary or ovarian cyst mucins (a generous gift from Dr. Elyin Kabat), as well as beads coated with A-active glycolipids as described previously by Clausen et al., *Molec, Immun.* 25:199-204, 1988. After vortexing, the mixture was incubated at room temperature for 1-2 hours. The microparticles were then centrifuged (3,000×g, 10 min.), washed with phosphate-buffered saline (PBS), blocked with either bovine serum albumin (BSA)/PBS 5% or human serum (1:10 dilution), and brought to final volume of 0.25% w/v in PBS. Antigen-coated particles were then diluted 1:10 in BSA-coated particles (similar procedure) to give a final particle concentration of 0.225% BSA particles and 0.025% transferase particles. Twenty µl of BSA-transferase or BSA-coated particles were distributed in 96-well Epicon assay plates (Pandex) with a 0.2 µm filter. The automated particle concentrated fluorescence immunoassay screen machine (Pandex) (as described in Jolley et al., *J. Immuol. Meth.* 67:21-35, 1984) performed the following steps sequentially by vacuum suction through the 0.2 µm filter in the bottom of each well and distribution of buffers through an 8-channel pump: incubation for 10 min with 50 µl of MAb culture supernatant, washing with PBS, incubation for 10 min. with 25 µl of affinity-purified goat anti-mouse Ig FITC-conjugated antibody (1:200, Pandex), washing with PBS, and reading at 485 mm/535 nm after final suction centering and concentrating antigen-coated particles in the bottom of wells.

C. Immunostaining of Cell Lines and Tissues

Cells were grown in media according to American Type Culture Collection (ATCC) guidelines, harvested by rubber policeman, and air-dried onto 10-well microslides (Carbon Scientific, Peokone, Ill.) for 2 hours. Slides were "fixed" in ice-cold acetone for 10 minutes and allowed to dry. Cells were incubated with primary antibody for 45 minutes at 37° C., washed with PBS, and incubated with fluorescein-conjugated rabbit anti-mouse antibody (Dakopatts, Denmark) for 30 minutes at 37° C. Similarly, human buccal mucosal tissues, salivary glands, and human intestine obtained at surgery were quick-frozen in isopentane precooled with dry ice, sectioned with a cryostat after embedding in Tissue-Tek ® (Miles Scientific), and processed immediately for immunostaining. Sections were air-dried briefly and "fixed" in acetone and immunostained as described "fixed" in acetone and immunostained as described for cell lines, except primary antibodies were incubated for 4 hours or overnight at 4° C.

Slides were examined in a Zeiss fluorescence microscope using epi-illumination. The microscope was equipped with FITC interference filters and a 200W Mercury lamp. For control of the staining, primary antibody was replaced with PBS or MAbs of other specificities but with the same isotype as the test antibody. Staining with the MAbs was also performed after "fixation" with paraformaldehyde or glutaraldehyde on air-dried slides and on cells grown as tumors in nude mice, which were fixed, paraffin-embedded, and sectioned. In the case of colonic tissues, sections were stained by avidin-biotin-peroxidase complex as previously described by Orntoft et al., *Lab. Invest.* 58:576-583, 1988.

D. Immunoprecipitation Of A Transferase Activity

One mg of affinity-isolated goat anti-mouse IgG (Boehringer Mannheim Bio-chemicals) was added to 10 ml of 1% Fluoricon Polystyrene Assay Particles (0 85 µm, Pandex) in PBS. After two hours at room temperature, the suspension was centrifuged (3,000×g) for 10 minutes, blocked with 3% BSA in PBS and resuspended to a final concentration of 1% w/v. Goat anti-mouse particles were mixed with MAb hybridoma supernatants in a 1:5 ratio, incubated at 4° C. for 15 minutes, and centrifuged (3,000×g) for two minutes. The beads were washed with Buffer A (50 mM Tris buffer [pH 7.4], 100 mM NaCl, 20 mM $MnCl_2$, 1 mM ethylenediaminetetraacetic acid, 0.1% Titron X-100, and 3% BSA), and resuspended in Buffer A to a concentration of 1%. Particles were added to enzyme samples to a concentration capable of binding to twice the amount of A transferase present (about 100 µl particles for 500 µl concentrated plasma). After 30 minutes at 4° C., the particles were centrifuged at 3,000×g for two minutes and the supernatant was assayed for remaining enzyme. The precipitated particles were washed twice with Buffer A, resuspended in 50 µl wash buffer, and assayed for enzyme activity. The transferase used was either purified or semipurified from human blood group A lungs, or from blood group A1, $A_2$, B or O plasma concentrated 10×by 30%–50% ammonium sulfate precipitation followed by concentration in an Amicon stirred cell membrane concentrator. Fucosyltransferase was from a Triton CF-54 homogenate of Colo205 cells after centrifugation at 100,000×g for one hour.

E. Inhibition of Transferase Activity by MAbs

Purified anti-A transferase MAbs, irrelevant MAbs with the same isotype, commercially obtained $IgG_1$ myeloma standard, or 20 mM Tris buffer (pH 7.4) were added to transferase preparations and incubated at 4° C. for 30 minutes. The enzyme activity of this mixture was then measured by incubation with reaction mixture at 37° C. for 10 or 30 minutes.

Example 4

Cloning and Characterization of DNA Complementary to Histo-Blood Group A Transferase mRNA A. Preparation of Synthetic Oligodeoxynucleotide Probes According to Partial Amino Acid Sequence Data Based on amino acid sequences of a few peptides released on Achromobacter endolysyl peptidase treatment or cyanogen bromide cleavage (described in Example 2), synthetic olig odeoxynucleotides were prepared with an Applied Biosystems DNA Synthesizer 380B.

B. RNA and DNA Preparation

Total RNA was prepared by the guanidine-HCl method (e.g., Winter et al., *J. Cell Biol.* 101:175–181, 1985; *Proc. Natl. Acad. Sci. USA* 82:7575–7579, 1985). In brief, cell pellets were homogenized in guanidine-HCl solution and ethanol-precipitated twice. After resuspension in a saline/SDS mixture, RNA was extracted with phenol and Seavag's mixture (chloroform/isoamyl alcohol, 24:1), followed by ethanol precipitation. The poly A+ fraction was selected by oligo-dT cellulose column chromatography (Maniatis et al., *Molecular Cloning: A Laboratory Manual*, 1982, Cold Springs Harbor Laboratory, New York). Genomic DNA was purified by digesting the tissues with proteinase K in the presence of SDS and EDTA, followed by extraction with Seavag's mixture and ethanol precipitation (Id.).

C. cDNA Libraries

All reagents and enzymes for cDNA synthesis were from the Promega cDNA synthesis kit and were used as per the manufacturer's instructions. cDNA was synthesized with MKN45 poly A+ RNA by the method of Gubler and Hoffman (*Gene* 25:263–269, 1983) using a random hexamer, instead of oligo-dT, as a primer. The cDNA was ligated with a phosphorylated Eco RI linker, digested with Eco RI, and electrophoresed on 1% agarose gel. The cDNA was size-selected (>1.3 bkb) and recovered from the gel by the PI method (Volgelstein and Gillespie, *Proc. Natl. Acad Sci. USA* 76:615, 1979), then ligated to the dephosphorylated Eco RI arms of the λgt10 vector. The ligated DNA was packaged in vitro with Stratagene's Giga Pack Gold packaging extract.

D. Screening of λgt10 Library

1. PCR Presence Test (cDNA) and PCR Identification Test (DNA From the Candidate Phase Clones). The polymerase chain reaction (PCR) (Saiki et al, *Science* 230:1350–1354, 1985; Saiki et al., *Science* 239:487–491, 1988) was performed using two degenerate synthetic oligos FY-1 and FY-2 (FIG. 1) as primers with TAq DNA polymerase. The reagents and enzyme were purchased from Perkins Elmer Cetus. Thirty-five cycles of denaturation (94° C.; 2 min), annealing (50° C.; 2 min.), and DNA polymerization (72° C.; 3 min.) were performed on the cDNA of MKN45 poly A+ RNA. The final 72° C. incubation was for 10 minutes. The product was electrophoresed on a 5% polyacrylamide gel and electrotransferred onto a Nylon membrane (Amersham). The membrane was baked at 80° C. under vacuum and probed for the internal sequence with a $^{32}$P-kinase-labeled oligodeoxynucleotide probe (FY-3). Presence of a hybridized band of expected length was considered a positive test.

2. Screening. Amplified fragment (98 bp) from the PCR presence test was gel-purified and used to screen the cDNA library. The positive plaques were cloned after the screening and DNA was prepared and analyzed by the PCR identification test.

E. Northern and Southern Hybridizations

Fifty μg RNAs or 5 μg poly A+ RNAs were electrophoresed through a denaturing formaldehyde-agarose gel and transferred onto a Nylon membrane. Eight μg genomic DNA was digested overnight with the appropriate restriction endonuclease and loaded onto a 1% agarose gel. After electrophoresis, the gels were denatured (30 min.) in 0.5N NaOH and 1.5M NaCl, neutralized (30 min., 2×) in 0.5M Tris-HCl (pH 7.5) 3M NaCl, and the DNA was transferred onto a Nylon membrane by capillary action (Maniatis et al., *Molecular Cloning: A Laboratory Manual*, 1982, Cold Springs Harbor Laboratory, New York). Both Northern and Southern filters were prehybridized in 50% formamide, 5×SSPE, 5×Denhardt's, and 0.1% SDS solution at 42° C. for two hours and then hybridized overnight at 42° C. with a $^{32}$P random primed-labeled (Feinberg and Vogelstein, *Anal. Biochem.* 132:6, 1983; *Anal. Biochem.* 137:266, 1984) probe from FY-59-5 insert. Filters were washed in 2×SSC, 0.1% SDS at room temperature three times and then in 1×SSC, 0.1% SDS at 68° C. for one hour. Final wash was in 0.1×SSC, 0.1% SDS at 68° C. for one hour.

F. Subcloning and Restriction Enzyme Mapping

DNA from the phage clones was digested with Eco RI and ligated with dephosphorylated Eco RI arms of pT7T3 plasmid (Pharmacia) or Phagescript SK (Stratagene). After DNA transformation of XL-1 Blue strain bacteria, the clones with insert were screened by color selection with IPTG and X-gal. Restriction enzymes were obtained from BRL or New England Biolabs.

G. DNA Sequencing

Dideoxynucleotide termination sequencing reactions (Sanger et al., *Proc. Natl. Acad. Sci. USA* 74:5463–5467, 1977) were performed with single-strand DNA of Phagescript clones or pT7T3 clones obtained by superinfection with helper phage. M13 universal primer and several synthetic oligodeoxynucleotide primers were used. The sequencing strategy is shown in FIG. 2. DNA sequencing was done using Sequenase (United States Biochemical Corp.), Klenow enzyme (BRL Kilobase system), and, for ambiguous regions, Taq DNA polymerase (Promega). IBI Pustell Sequence Analysis Software (MS-DOS version) was used for sequence analysis.

Example 5

Construction of A and B Transferase cDNA Expression Constructs cDNAs (FY-66-1, and FY-69-3) were excised from pT7T3 plasmid (Pharmacia LKB Biotechnology; Piscataway, N.J.) constructs. FY-59-5/66-7 was constructed by replacing Hind III (in the polylinker sites)-Sst II fragment containing the N-terminal half of the coding region of FY-66-7 in pT7T3 plasmid by that of FY-59-5, creating cDNA with intact coding region of FY-59-5 and shorter 3' untranslated sequence. Another construct, FY-66-1/59-7/66-1, was constructed by replacing the Bst EII-Sst II fragment of FY-66-1 by that of FY-59-7. These cDNA inserts were excised by Eco RI digestion, gel purified and inserted into dephosphorylated Eco RI site of pSG-5 vector in either orientation.

Sst II-Ava I vector fragment was purified by digesting p59-5/66-7(s) fragment with Sst II, Ava I, and Bss HII, and extracting DNA from 1% agarose electrophoresed gel fragment by the potassium iodide method according to Vogelstein and Gillespie (*Proc. Natl. Acad. Sci. USA* 76:615, 1979). All the Sst II-Ava I inserts were prepared by digestion with Sst II and Ava I and extraction by the same method. These inserts were further digested and electrophoresed through 2% agarose gel for chimera constructions. Gel fragments were excised and combined, DNA was extracted, and this mixture of two fragments was ligated with purified Sst II-Ava I vector portion. The DNA was then used to transform E. coli XL-1 blue strain competent bacteria. DNA from transformants was purified in mini-scale and analyzed by diagnostic restriction enzyme digestion. The candidate clones were cultured in large-scale and DNA was purified and analyzed for substitutions (Bss HII, Alu I, and Bst NI for the first, second, and third substitutions). For the fourth substitution, two allele-specific oligodeoxynucleotides (fy-67 (Sequence ID No. 17): CCCGAAAGAACCCCCCCA for A allele, and fy-68 (Sequence ID No. 18): CCCGAAGAACGCCCCCA for B allele) were synthesized and used for dot blot screening of plasmid DNAs. Sst II-Bam HI vector fragment of these chimera was replaced by that of p66-1(s) to introduce an intron. All of the constructs were further confirmed by sequencing.

The final constructs had the same sequence except for differences in specific nucleotides, some of which resulted in differences in deduced a.a. sequence at four locations (a.a. 176, 235, 266, and 268). Since the other nucleotide substitutions were conservative changes (i.e., did not result in a.a. substitutions), all the chimera constructs were named based on status at these four locations. The names of the constructs and their origins of Sst II-Ava I are shown in Table 4. Expression construct pAAAA is the construct which has the predicted a.a. sequence (arginine, glycine, leucine, glycine) of A transferase at these sites. Similarly, pBBBB has the predicted a.a. sequence (glycine, serine, methionine, alanine) of B transferase at these sites. Because of an apparent partial digestion problem of Mbo II, three constructs (pAABA, pBABA, and pBBBA) were prepared by ligating each Sst II-Fok I fragment with Fok I-Ava I fragment of a previously-made construct (pABBA).

Laboratory Manual, Cold Spring Harbor Laboratory, N.Y., 1982) followed by polyethylene glycol adsorption (PEG method) (Krieg and Melton, Nucleic Acid Res. 2:7057, 1984). The DNA was further purified by extracting with phenol-SEAVAG mixture and ethanol precipitation to remove PEG and residual E. coli proteins, which are toxic for the cultured cells. DNA prepared in this way was shown to be clean enough to function in DNA-transfected cells (Yamamoto and Perucho, Oncogene Res. 3:125, 1988). DNA transfection was performed as described by Chen and Okayama (Mod. Cell. Biol. 1:2745, 1987) using a DNA transfection kit from Stratagene. Briefly, HeLa cells were inoculated at a density of 2–3×100,000 cells per plate in DMEM plus 10% FCS, and cultured overnight. The medium was replaced 8 hours prior to DNA addition. 20 µg of plasmid DNA was resuspended in 450 µg of sterile $H_2O$ and mixed with 50 µg of 2.5M $CaCl_2$ solution. 500 µl of 2×BBS (N,N-bis(2-hydroxyethyl)-2-aminoethanesulfonic acid and buffered saline) (pH 6.95) was added and left at room temperature for 20 minutes. The mixture was added drop-wise onto the culture medium. Cells were inoculated at 35° C. with 3% $CO_2$ overnight, transferred in the incubator at 37° C. with 5% $CO_2$ next day after medium change, further cultured for 72 hours, and harvested with trypsin-EDTA treatment. Trypsin was inactivated by DMEM supplemented with 10% FCS, and FCS was removed by washing with PBS saline. Finally, the cells were fixed with 1.5% pareformaldehyde in PBS for 30 minutes and resuspended in 600 µl of PBS plus 5% FCS and 0.05% $NaN_3$.

B. Immunostaining

Cells (200 µl cell suspension) were first immunostained with 100 µl of anti-A or anti-B murine MAb mixture (Ortho Diagnostics Inc., Raritan, N.J.) on ice for 1 hour. After washing with PBS, cells were stained with a mixture of rabbit and goat FITC-conjugated anti-mouse immunoglobulin (Ig) antibodies (100 µl of

TABLE 4

A-B Transferase cDNA Chimeras

| Name of construct | Fragment(s) and its origin | |
|---|---|---|
| p59-5/66-7 | SstII-A-(BstYI)-A-(FokI)-A-(MboII)-A-AvaI | |
| p69-3 | SstII-B-(BstYI)-B-(FokI)-B-(MboII)-B-AvaI | |
| pAAAA | SstII-A-A-A-A-AvaI (p59-5/66-7) | |
| pBBBB | SstII-B-B-B-B-AvaI (p69-3) | |
| pAABB | SstII-A-A-FokI (pAAAA) | FokI-B-B-AvaI (pBBBB) |
| pBBAA | SstII-B-B-FokI (pBBBB) | FokI-A-A-AvaI (pAAAA) |
| pABBB | SstII-A-BstYI (pAAAA) | BstYI-B-B-B-AvaI (pBBBB) |
| pBAAA | SstII-B-BstYI (pBBBB) | BstYI-A-A-A-AvaI (pAAAA) |
| pABAA | SstII-A-BstYI (pAABB) | BstYI-B-A-A-AvaI (pBBAA) |
| pBABB | SstII-B-BstYI (pBBAA) | BstYI-A-B-B-AvaI (pAABB) |
| pAAAB | SstII-A-A-A-MboII (pAAAA) | MboII-B-AvaI (pAABB) |
| pABAB | SstII-A-B-A-MboII (pABAA) | MboII-B-AvaI (pBABB) |
| pBAAB | SstII-B-A-A-MboII (pBAAA) | MboII-B-AvaI (pABBB) |
| pBBAB | SstII-B-B-A-MboII (pBBAA) | MboII-B-AvaI (pBBBB) |
| pABBA | SstII-A-B-B-MboII (pABBB) | MboII-B-AvaI (pBAAA) |
| pAABA | SstII-A-A-FokI (pAABB) | FokI-B-A-AvaI (pABBA) |
| pBABA | SstII-B-A-FokI (pBABB) | FokI-B-A-AvaI (pABBA) |
| pBBBA | SstII-B-B-FokI (pBBBB) | FokI-B-A-AvaI (pABBA) |

Example 6

Expression of A and B Transferase Activities in DNA Transfected HeLa Cells

A. DNA Transfection

Plasmid DNA was prepared by SDS-alkaline denaturation method (Maniatis et al., Molecular Cloning: A Laboratory Manual, Cold Spring Harbor Laboratory, 100×diluted in PBS; Sigma Chemical Co., St. Louis, Mo.) on ice for 1 hour. Cells were washed with PBS and resuspended in the same buffer described above and FACS analyzed using an EPICS PROFILE machine (Courier; Hialeah, Fla.).

C. Expression of A and B Transferase Activities in DNA Transfected HeLa Cells The results of three independent experiments are shown in Table 5. The numbers show the percentages of positive cells determined by FACS analysis. None of the anti-sense constructs ("as") could induce A or B antigens. Transfection of p59-5/66-7(s) DNA showed some A antigen positive cells, but that of p66-1(s) was more effective. Both alleles of HeLa cells were found to have a single base deletion common among O alleles and, thus, the genotype of HeLa cells at the ABO locus is OO.

TABLE 5

Expression of histo-blood group A and B antigens on HeLa cells transfected with cDNA expression DNAs

| Plasmid DNA | exp. 1 A | exp. 1 B | exp. 2 A | exp. 2 B | exp. 3 A | exp. 3 B | Activity |
|---|---|---|---|---|---|---|---|
| p59-5/66-7(s) | 0.9 | 0.0 | 0.6 | 0.1 | 5.7 | 0.0 | A |
| p59-5/66-7(as) | 0.0 | 0.0 | 0.0 | 0.1 | 0.0 | 0.0 | — |
| p66-1(s) | 1.4 | 0.0 | 3.9 | 0.1 | 14.8 | 0.0 | A |
| p66-1(as) | 0.0 | 0.0 | 0.0 | 0.0 | 0.0 | 0.0 | — |
| no DNA | 0.0 | 0.0 | 0.0 | 0.0 | 0.0 | 0.0 | — |

D. Expression of A and B Transferase Activities in Cells Transfected with A-B Transferase Chimeric cDNAs Results of three independent DNA transfection experiments are shown in Table 6. The numbers indicate percentages of cell populations positively stained with antibody as described. NT signifies not tested. Although the values vary among experiments, overall results are similar. Constructs in one group (pAAAA, pAAAB, pABAA, pBAAA, pBAAB, and pBBAA) encode a protein with A transferase activity. Constructs in a second group (pAABB, pABBB, pBABB, and pBBBB) encode a protein with B transferase activity. Constructs in the third group (pAABA, pABAB, pABBA, pBABA, pBBAB, and pBBBA) encode an enzyme with A and B transferase activities.

TABLE 6

Expression of histo-blood group A and B antigens on HeLa cells transfected with DNA of A-B transferase cDNA-chimera constructs

| Plasmid DNA | exp. 1 A | exp. 1 B | exp. 2 A | exp. 2 B | exp. 3 A | exp. 3 B | Activity |
|---|---|---|---|---|---|---|---|
| pAAAA | 41.5 | 0.0 | 3.8 | 0.0 | 14.0 | 0.1 | A |
| pAAAB | 17.5 | 0.3 | 1.2 | 0.0 | 7.4 | 0.1 | A |
| pAABA | NT | NT | 1.0 | 0.6 | 2.4 | 1.1 | AB |
| pAABB | 0.2 | 26.3 | 0.1 | 1.4 | 0.1 | 5.6 | B |
| pABAA | 27.5 | 0.2 | 5.7 | 0.1 | 11.6 | 0.1 | A |
| pABAB | 21.3 | 3.0 | 1.8 | 0.1 | 5.8 | 0.2 | A(B) |
| pABBA | 17.0 | 22.1 | 0.8 | 1.4 | 2.1 | 2.9 | AB |
|  |  |  | 0.6 | 0.9 |  |  |  |
| pABBB | 0.1 | 31.1 | 0.1 | 1.6 | 0.1 | 5.5 | B |
| pBAAA | 29.1 | 0.1 | 2.9 | 0.1 | 10.3 | 0.0 | A |
| pBAAB | 10.0 | 0.1 | 0.5 | 0.0 | 4.8 | 0.1 | A |
| pBABA | NT | NT | 0.5 | 0.4 | 3.1 | 1.3 | AB |
| pBABB | 0.1 | 20.7 | 0.0 | 1.0 | 0.0 | 5.4 | B |
| pBBAA | 12.7 | 0.1 | 4.8 | 0.0 | 12.3 | 0.0 | A |
| pBBAB | 29.5 | 2.9 | 1.4 | 0.0 | 8.0 | 0.4 | A(B) |
| pBBBA | NT | NT | 1.0 | 0.6 | 3.2 | 2.0 | AB |
|  |  |  | 0.7 | 0.4 |  |  |  |
| pBBBB | 0.1 | 30.6 | 0.0 | 2.5 | 0.1 | 3.3 | B |
| no DNA | 0.0 | 0.1 | 0.0 | 0.0 | 0.0 | 0.0 | — |

Example 7
Genotyping by Diagnostic Restriction Enzyme Digestion

A. Identification of Allele-Specific Restriction Sites

Genomic DNAs were prepared by proteinase K-SDS method (T. Maniatis et al., *Molecular Cloning: A Laboratory Manual*, 2d Ed., Cold Spring Harbor Laboratory, N.Y., 1989). Nucleotide sequence analysis of cDNA clones identified allele-specific restriction enzyme cleavage sites at three of the four substitutions between A and B allelic cDNAs, as well as the single-base deletion found in O allelic cDNAs (FIG. 6A). The single-base deletion associated with the predicted O alleles (position 258) creates a KpnI site (O allele) and eliminates the BstEII site (A/B allele). Three of the four nucleotide substitutions between A and B allelic cDNAs can also be defined by diagnostic restriction enzyme. The substitution at position 523 changes BssHII (A allele) to NarI (B allele), at position 700 HpaII (A allele) to AluI (B allele) and at position 793 Bst NI (A allele) to NlaIII (B allale ).

Analysis of PCR-amplified DNA

PCR reaction was performed with 1 μg of DNA with Taq DNA polymerase with a DNA Thermal Cycler (Perkin Elmer Cetus, Norwalk, Conn). The synthetic oligodeoxynucleotides used are: fy-29 (Sequence ID No. 19), 5'-CGTTCTGCTAAAACCAAG; fy-31 (Sequence ID No. 20), 5'-GAAATCGCCCTCGTCCTT; fy-43 (Sequence ID No. 21), 5'-GGATCCAGGGGT-GCACGGCCGGCGGC; fy-47 (Sequence ID No. 22), 5'-TGCTGGAGGTGCGCGCCTAC. Primers fy-43 and fy-31 were used for amplification in (b), and fy-29 and fy-47 in (c). The BamHI site in fy-43 is artificial. There were 35 cycles of reaction (denaturation at 94° C. for 90 s, annealing at 50° C. for 2 min., and incubation at 72° C. for 3 min. with 5 s extension for each cycle). The samples were extracted with phenol-(chloroform:isoamyl alcohol, 24:1), ethanol-precipitated and resuspended in 20 μl of 1 mM Tris (pH 7.5), 1 mM EDTA. Next, 5 μl of the DNA was digested with restriction enzymes and subjected to 12% PAGE. The gels were stained with ethidium bromide and photographed.

The two pairs of primers (fy-43 and-31, and fy-47 and -29) described above were satisfactory for PCR amplification of fragments ( 467 and 621 base pairs respectively) which cover the four important base substitutions between A and B genes. The cleavage sites susceptible to diagnostic restriction enzymes were detected by the presence of fragments in 12% polyacrylamide gels, stained by ethidium bromide to detect the first (FIG. 6B) and second (FIG. 6C) differences between A and B alleles. The NarI fragments of 205 and 262 base pairs (bp) were obtained with DNA from SW48 (lane 3) and SW1417 (lane 5, FIG. 6B). The 203- and 264-bp fragments were obtained after digestion with BssHII of DNA from all the cell lines examined, but the 467-bp fragment remained for SW48 (lane 8) and SW1417 (lane 10, FIG. 6B), indicating heterozygosity of these cells for BssHII (A allele) and NarI (B allele) at this position. The other cell lines, MKN45 (lane 6), SW948 (lane 7) and COLO205 (lane 9) were homozygous for BssHII (A allele). Similarly, as shown in FIG. 6C, SW48 and SW1417 were found to be heterozygous for HpaII (A allele; lanes 8 and 10 ) and AluI (B allele; lanes 3 and 5 ). The other cell lines were homozygous at this second site for HpaII. These results confirmed the presence of these nucleotide differences in genomic DNA as well as cDNA.

C. Southern Hybridization

Southern hybridization was performed with 10 μg of DNA. DNA was electrophoresed through 1% agarose gel after digestion with BstEII or KpnI and transferred onto Nylon membrane (Amersham Corp., Arlington Heights, Ill.). The filter was baked and prehybridized in 50% formamide, 5×SSPE, 5×Denhardt's, and 0.1% SDS solution at 42° C. (2 h) and then hybridized overnight at 42° C. with a [$^{32}$P] random prime-radiolabeled probe from the FY-59-5 insert. The filter was washed in 2×SSC, 0.1% SDS at room temperature three times and the 1×SSC, 0.1% SDS at 68° C. (1 h). Final wash was in 0.1×SSC, 0.1% SDS at 68° C. DNA markers are phi-X/HaeIII (phi) and pBR 322/MspI (pBR).

The single base deletion found in O allelic cDNA was detected in genomic DNA by Southern blot analysis (FIG. 6D). Restriction enzyme digestion with BstEII (lanes 1-5) and KpnI (lanes 6-10) of genomic DNA from the five cell lines followed by Southern transfer and hybridization with FY-59-5 insert probe confirmed the finding of the present invention of a single base deletion in genomic DNA. In addition, homozygosity for this deletion was detected in two O cell lines. The MKN 45 cell line (lanes 1 and 6) was homozygous for the BstEII site, or without deletion. SW948 (lanes 2 and 7) and COLO 205 (lanes 4 and 9) were homozygous for the KpnI site. The SW1417 cell line (lanes 5 and 10) was heterozygous.

D. Analysis of Genomic DNAs From Blood Samples

Genomic DNAs from blood samples (bully coat) of different ABO phenotype were also analyzed. DNAs from bully coat fraction of blood samples with clearly defined ABO phenotypes were analyzed as described in sections B and C above. Status is represented by the diagnostic restriction enzyme cleavage site specific for each allele. Status at position 1 was determined for the presence of single base deletion by Southern blot analysis after BstEII or KpnI digestion. Status at positions 2 and 3 was determined by PCR and restriction enzyme digestions (NarI/BssHII and AluI/HpaII) for positions 2 and 3, respectively. Genotype was inferred from status at these sites, and from phenotype. As shown in Table 7, all four O samples had the single base deletion (at position 1) in both alleles. All the A and B samples showed at least one functional allele, devoid of the single base deletion. The AB samples showed two functional alleles. All of the B and AB samples tested showed the presence of NarI and AluI sites (at position 2 and 3, respectively).

TABLE 7

Genotyping of Genomic DNA From Blood Samples at ABO locus[a]

| Specimen No. | Blood Phenotype | Status At Position 1 (nucleotide 258) | Status At Position 2 (nucleotide 523) | Status At Position 3 (nucleotide 700) | Genotype |
| --- | --- | --- | --- | --- | --- |
| 1 | A | —/— | A/A | A/A | AA |
| 2 | A | O/— | A/A | A/A | AO |
| 3 | A | O/— | A/A | A/A | AO |
| 4 | B | O/— | A/B | A/B | BO |
| 5 | A | O/— | A/A | A/A | AO |
| 6 | O | O/O | A/A | A/A | OO |
| 7 | O | O/O | A/A | A/A | OO |
| 8 | O | O/O | A/A | A/A | OO |
| 9 | O | O/O | A/A | A/A | OO |
| 10 | AB | —/— | A/B | A/B | AB |
| 11 | B | O/— | A/B | A/B | BO |
| 12 | B | O/— | A/B | A/B | BO |
| 13 | B | O/— | A/B | A/B | BO |
| 14 | AB | —/— | A/B | A/B | AB |

[a]The dash (—) indicates the non-O (BstEII-cleavable, KpnI-uncleavable) allele at this position. O/—, a combination of KpnI-cleavable O allele and non-O allele. A, BssHII cleavable allele at position 2, or HpaII cleavable allele at position 3. B, NarI-cleavable allele at position 2, or AluI-cleavable alele at position 3. A/A and A/B, combination of these alleles at each position.

Example 8

Histo-Blood Group A$^2$ Subtype

A. Polymerase Chain Reaction and Direct Nucleotide Sequencing

PCR (Saiki et al., Science 230:1350-1354, 1985) was performed per manufacturer's protocol, using a DNA-Thermal Cycler from Perkin-Elmer Cetus (Norwalk, Conn.). One μg of genomic or 0.5 μg of cDNA was used as template for the amplification reaction. Genomic DNA was prepared by the SDS-Proteinase K method (Maniatis et al., Molecular Cloning: A Laboratory Manual, Cold Spring Harbor Laboratory, N.Y., 1982) using 10 ml of a buffy coat fraction of human blood (American Red Cross, Portland, Oreg.) which had been washed twice with the same volume of phosphate buffered saline (PBS). Proteinase K was obtained from BRL (Gaithersburg, Md.). cDNA was synthesized with poly A+RNA by the method of Gubler and Hoffman (Gene 25:263-269, 1983) using a Riboclone cDNA synthesis system (Promega Corporation, Madison, Wis.). Poly A+RNA was isolated with a FastTrak mRNA isolation kit per manufacturer's protocol (Invitrogen, San Diego, Calif.). Nine ml of buffy coat fraction was mixed with 27 ml of PBS, loaded onto 12 ml of Ficoll, and centrifuged at 2000 r.p.m. for 25 min. The lymphocyte fraction was recovered, washed with PBS twice, and used for poly A+RNA preparation.

Oligodeoxynucleotides were synthesized with an Applied Biosystems 380B DNA synthesizer. The pairs of synthetic oligodeoxynucleotide primers used were: fy-88 and fy-39, fy-73 and fy-38, fy-74 and fy-31, and fy-47 and fy-78. The nucleotide sequences of these oligos are: fy-88 Sequence ID No. 23, CGGAATTCGAGACCAGACCGGAGCC; fy-39 (Sequence ID No. 24, CCTGAACTGCTCGTTGA; fy-73 (Sequence ID No. 25, TGCCAGCTCCATGTGACCGC; fy-38 (Sequence ID No. 26, GAGCTCAGTAAGATGCT;

fy-74 (Sequence ID No. 27, GCGGCTCCCCCAGCCCCCGT; fy-31 (Sequence ID No. 20, GAAATCGCCCTCGTCCTT; fy-47 (Sequence ID No. 22, TGCTGGAGGTGCGCGC-CTAC; fy-78 (Sequence ID No. 30, CCGGATCCGTGTGATTTGAGGTGGGGAC. Both the Eco RI site in fy-88 and Bam HI site in fy-78 are artificial. Five μl of one and 0.5 μl of another 20 pmol/μl oligos were added to the heat-denatured DNA, followed by addition of the reaction mixture (45 μl H$_2$O, 10 μl 10×reaction buffer, 16 μl 1.25 mM dNTP mixture, and 1 μl 2.5 units/μl Taq DNA polymerase) for disproportional PCR. Taq DNA polymerase was purchased from Perkin-Elmer Cetus (Norwalk, Conn.). Nested PCR technique was also used in some amplification. Two drops of paraffin oil were overlaid to prevent evaporation. Amplification was performed by stepcycle mode of 40 rounds of 94° C. 2 min, 50° C. 2 min, and 70° C. 3 min, followed by one round of 94° C. 2 min, 50° C. 3 min, and 70° C. 10 min, and samples were left at 10° C. until processing. Amplified DNA was extracted with 100 μl phenol:chloroform:isoamyl alcohol mixture (25:24:1), and the aqueous fraction was transferred into Eppendorf tubes with 100 μl 14M ammonium acetate and 200 μl isopropanol. After centrifugation, the pellet was washed with 70% ethanol, dried, and resuspended in H$_2$O.

DNA sequencing was performed with TaqTrak sequencing system per manufacturer's protocol (Promega Corporation). Twenty pmol of synthetic oligodeoxynucleotides were end-labeled with T4 polynucleotide kinase and $\gamma$-$^{32}$P labeled ATP (Amersham Corp., Arlington Heights, Ill.) as donor. Two pmol of the labeled primer and amplified fragment were heated at 95° C. for 5 min, followed by snap cooling on ice; this mixture was used for Sanger dideoxy termination method (Sanger et al., *Proc. Natl. Acad. Sci. USA* 74:5463-5467, 1977).

Two pairs of primers (fy-74 and fy-31, and fy-47 and fy-78) were used to amplify the genomic DNA containing the last coding exon (C-terminal catalytic domain). The corresponding sequence for primer fy-74 resides in the intron preceding this exon (the last base of fy-74 locates 16 base 5' side of the splicing acceptor site), and that of fy-78 in the 3' untranslated region (the last base of fy-78 locates 127 base 3' side of the termination codon). Primers fy-47 and fy-31 are homologous to the sequences in the last exon, and the amplified fragments by these oligo pairs overlap each other. The primers fy-73 and fy-38 were used to amplify the genomic DNA to cover the preceding exon (the last bases of fy-73 and fy-38 locate 28 base 5' side of splicing acceptor site and 146 base 3' side of splicing donor site, respectively). Most of the coding region of the soluble form of A transferase (274 a.a.s out of 301) is contained in these two exons. The genomic DNA from bully coat fraction of human blood with two different blood types, A$_1$B and A$_2$, was used for PCR and direct sequencing. The sequencing reaction samples were electrophoresed side by side to facilitate detection of differences, because direct sequencing reveals the sequence mixture of both alleles; the results are usually not so clear as those with single-stranded phage and denatured plasmid DNAs.

Comparison of the deduced a.a. sequence of A$^2$ allele corresponding to the soluble form of A$^1$ transferase, and the partial nucleotide sequences containing the important difference, are shown in FIGS. 7 and 8. Comparison of the nucleotide sequence of A$^2$ allele from an A$^2$O individual with that of A$^1$ allele from an A$^1$B individual revealed only two differences; one single base substitution and one single nucleotide deletion. The nucleotide substitution (T in A$^2$ and C in A$^1$ at nucleotide position 467 from initiation codon) results in the a.a. substitution (leucine in A$^2$ transferase and proline in A$^1$ transferase at a.a. position 156). The same single base substitution was previously found in FY-59-5 eDNA clones, and the resulting a.a. substitution was found to be incapable of drastically altering enzymatic activity or sugar-nucleotide donor specificity, based on observed expression of chimeric cDNAs in transfected HeLa cells (Example 6). The single nucleotide deletion was found in three stretches of Cs (nucleotide position 1059-1061 in A$^1$ allele). This single base deletion, located at the end of the C-terminal, changes the reading frame and results in a protein with 21 additional a.a.s (FIGS. 7 and 8).

The nucleotide sequence up to the corresponding nucleotide for alanine, at a.a. 54 of the N-terminal of the soluble form of A transferase was determined. No difference between A$^1$ and A$^2$ alleles was observed in this region of amplified fragments. DNA was prepared from buffy coat fractions of seven more A$_2$ individuals. PCR-amplified fragments from these genomic DNA samples were used for direct nucleotide sequencing, and the single nucleotide deletion was found in all samples. However, the same nucleotide substitution at a.a. 156 was also observed in all samples.

While the single base deletion is located close to the N-terminal in the O allele, that of A$^2$ allele is close to the C-terminal. As a result of frameshift, the O allele is unable to code for the functional glycosyltransferase, but the A$^2$ allele is able to code for the protein with 21 additional a.a.s, which is still functional although there are changes in activity strength and substrate specificity. Based on chimera constructions and DNA transfection experiments (described in Examples 5 and 6), a single a.a. substitution may change sugar-nucleotide donor specificity. The location of the a.a. substitutions suggests the importance of this region for interaction with sugar-nucleotide. The C-terminal may be important for the strength and acceptor specificity of enzymatic activity, although this could alternatively be due mainly to the steric hindrance of the additional 21 a.a.s. This approach (PCR and direct sequencing of amplified fragments) to elucidating the molecular basis of the A$^2$ allele may be applied to other subtypes and rare polymorphisms of the histo-blood group ABO system.

B. Introduction of Single Base Deletion Into A$^1$transferase cDNA Expression Construct A genomic DNA fragment from an A$_2$ individual was amplified by PCR as described above using two primers, fy-78 and fy-48 (Sequence ID No. 31) (TAC-TACCTGGGGGGGTTCTT), purified, and subjected to restriction enzyme digestion with Ava I and Bam HI. After electrophoresis, the gel fragment containing Ava I/Bam HI 251 bp DNA fragment was excised and DNA was extracted and ligated with Ava I/Bam HI vector fragment from A$^1$ transferase cDNA expression construct p59-5/66-7 (s) (see Example 5). This resulted in a decrease of 22 bp because of the size difference of the 3' untranslated region in these fragments. The nucleotide sequences of several recombinant clones were determined. Some of the clones had a single base deletion while others did not, which confirmed our direct sequencing results. These two types of clones differed only in this single base deletion. Both possessed the single base substitution because the backbone construct was derived from FY-59-5. Therefore, these two constructs were compared in terms of their expression in the DNA-transfected HeLa cells. In order to standardize the efficiency of DNA transfection, 5 μg of pBBBB plasmid DNA (Example 5) was added to 15 μg of test DNA and used for DNA transfection.

C. DNA Transfection and Immunodetection of Expression

DNA transfection was performed (as described in Example 6) using HeLa cells as the recipient by CaPO$_4$-method. Three days after transfection, cells were recovered and subjected to immunostaining and FACS analysis (Table 8). The primary antibodies used were anti-A and anti-B murine monoclonal antibody mixtures (Ortho Diagnostics, Raritan, N.J.). FITC-conjugated goat anti-mouse immunoglobulin was used as the secondary antibody. In addition, cells were assayed for A transferase activity. The introduction of the single base deletion decreased A transferase activity 30–50 fold.

TABLE 8

FACS Analysis of Immunostained DNA-transfected Cells

| DNA | Positive cell % with anti-A | Positive cell % with anti-B | Adjusted ratio |
|---|---|---|---|
| pA$^2$ | 0.7 | 16.1 | 1.0 |
| pA$^2$ | 0.2 | 2.8 | 1.6 |
| pA$^1$ | 21.7 | 10.7 | 46.6 |
| pA$^1$ | 22.8 | 10.2 | 51.4 |
| no DNA | 0.0 | 0.0 | — |

DNA preparations from two different clones (1 and 2) of each construct were used for DNA transfection experiments. Plasmid pA$^2$ has the single base deletion while plasmid pA$^1$ does not; otherwise they are identical in nucleotide sequence. Taking into consideration that the efficiency of DNA transfection differs among samples, judged by the different positive cell % with anti-B antibody, the relative positive cell % with anti-A antibody was calculated and shown under "Adju sted ratio."

Example 9

Cloning of Homologous Genes

A. Purification of Genomic DNA

Human genomic DNA was prepared from buffy coat fraction of human blood (genotype OO and ABO locus) by Proteinase K-SDS method (maniatis et al., *Molecular Cloning: A Laboratory Manual*, Cold Spring Harbor Laboratory, N.Y., 1982). Proteinase K was obtained from BRL (Gaithersburg, Md.).

Synthetic Oligodeoxynucleotides

Oligos were synthesized with Applied Biosystems 380B DNA Synthesizer. The nucleotide sequences of oligos are: fy-81 (Sequence ID No. 32), CGGAATTCA(A/T)G(T/C)ACTTCATGGT(G/T)GGCCA; fy-82 (Sequence ID No. 33), CGGAATTCAG(-G/A)TGGCT(T/C)TC(G/A)TC(G/A)TGCCA.
Both Eco RI sites are artificial. The degenerate nucleotides shown in parentheses were used to represent both α1→3 galactosyltransferase and A and B transferases genes.

Polymerase Chain Reaction

PCR (Saiki et al., *Science* 230:1350–1354, 1985) was performed according to manufacturer's protocol using a DNA-Thermal Cycler from Perkin-Elmer Cetus (Norwalk, Conn.). One μg of genomic DNA was resuspended in 20 μl of H$_2$O and treated at 95° C. for 5 min. Five μl of 20 pmol/μl synthetic oligodeoxynucleotide primers were then added to the heat-denatured DNA, followed by addition of the reaction mixture (45 μl H$_2$O, 10 μl, 10X reaction buffer [500 mM KCl 100 mM Tris-HCl, pH 8.3, 15 mM MgCl$_2$, 0.1% (w/v) gelatin], 16 μl 1.25 mM dNTP mixture, and 1 μl of 2.5 units/μl Taq DNA polymerase from Perkin-Elmer Cetus). Two drops of paraffin oil were overlaid to prevent evaporation. Amplification was performed by step-cycle mode of 40 rounds of 94° C. for 2 min (denaturation), 50° C. for 2 min (annealing), and 70° C. for 3 min (extension), followed by one round of 94° C. for 2 min, 50° C. for 3 min, and 70° C. for 10 min. Samples were left at 10° C. until processing. Amplified DNA was extracted with 100 μl phenol:chloroform:isoamyl alcohol (25:24:1) mixture, and the aqueous layer was transferred into Eppendorf tubes with 100 μl 4M ammonium acetate and 200 μl isopropanol. After centrifugation, the pellet was washed with 70% ethanol, dried, and resuspended in H$_2$O.

Subcloning of PCR-amplified Fragments

After overnight digestion with Eco RI, the PCR reaction product was loaded onto a 2% agarose gel for size fractionation. After electrophoresis the gel fragment containing the amplified DNA of expected size (approximately 510 bp) was excised and DNA was gel-purified with Geneclean kit (Bio 101 Inc., La Jolla, Calif.). The DNA eluted from the glassmilk was used for ligation with Eco RI-digested, phosphorylated pT7T3U18 vector (Pharmacia-LKB, Piscataway, N.J.). After overnight ligation, the DNA was used to transform XL1-blue strain competent *E. coli* bacteria (Stratagene, La Jolla, Calif.). The IPTG=X-Gal color selection was used for detection of colonies with insert-containing plasmid. Plasmid DNA was prepared on a small scale and used to examine insert size. DNA was then alkaline-denatured for DNA sequencing. DNA from the important clones was later prepared on a large scale and used for extensive DNA sequencing.

E. Nucleotide Sequencing

For DNA sequencing of mini-prep denatured DNA, TaqTrak sequencing system was used with fy-81 as primer per manufacturer's protocol. For extensive sequencing of the large-scale purified DNA, Sequenase system (United States Biochemical, Cleveland, Ohio) as well as TaqTrak system (Promega Corporation) were used with fy-81, fy-82, T3, T7, and M13 primers. For TaqTrak sequencing, 50 pmol of synthetic oligodeoxynucleotides were end-labeled with T4 polynucleotide kinase and γ-$^{32}$P labeled ATP (Amersham Corp., Arlington Heights, Ill.) as a donor. Five pmol of the labeled primer and alkaline-denatured plasmid DNA were incubated at 42° C. for 10 min for annealing, and this mixture was used for Sanger's dideoxy termination method (15). For Sequenase sequencing of the purified plasmid DNA as well as single-stranded DNA prepared by superinfection with helper phage M13K07, $^{32}$P-dATP (Amersham Corp., Arlington Heights, Ill.) was added in the extension reaction.

F. PCR-labeled Probe Preparation

Inserts were gel-purified after electrophoresis of the Eco RI-digested plasmids with Geneclean kit and used for PCR amplification. PCR was done with the same reaction mixture described above except that $^{32}$P-labeled dATP and a low concentration of cold dATP were used. Thirty rounds of amplification (94° C. for 30 sec, 37° C. for 30 sec, and 70° C. for 3 min) were performed. After reaction, the amplified fragments were purified as described and used for hybridization experiments.

G. Southern Hybridization

Twelve μg of human genomic DNA was digested overnight with Eco RI, Hind III, or Bam HI and loaded onto a 1% agarose gel. After electrophoresis, the gel was denatured (30 min) in 0.5N NaOH and 1.5M NaCl, neutralized (30 min, 2×) in 0.5M Tris-HCl (pH 7.5) and 3M NaCl, and the DNA was transferred onto a Nytran membrane by capillary action (Maniatis et al., *Molecular Cloning: A Laboratory Manual*, Cold Spring Harbor Laboratory, N.Y., 1982). After baking, Southern filters were prehybridized in 50% formamide, 5×SSPE, 5×Denhardt's, and 0.1% SDS solution at 42° C. for 2 hr, then hybridized overnight at 42° C. with a $^{32}$P PCR-labeled probe from inserts from the representative clones. Filters were washed in 2×SSC, 0.1% SDS at room temperature three times and then in 1×SSC, 0.1% SDS at 68° C. for 1 hr. Final wash was in 0.1×SSC, 0.1% SDS at 68° C. for 1 hr.

H. Cloning of Homologous Genes

The PCR approach was employed using one pair of synthetic oligodeoxynucleotide primers whose sequences are well conserved in histo-blood group A and B transferases and α1→3 galactosyltransferases. The gel-purified PCR-amplified fragments of the expected size were cloned into the vector for DNA sequencing. Individual clones were classified based on nucleotide sequence. Groups representing α1→3 galactosyltransferase and ABH genes were thereby identified. In addition, another group of clones showing extensive sequence homology with these two groups was identified. The presence of this homologous sequence was confirmed by different patterns of Southern hybridization.

The strategy for PCR cloning of homologous genes is shown schematically in FIG. 9. The regions corresponding to the two primers are well conserved between α1→3 galactosyltransferase (Joziasse et al. *J. Biol. Chem.* 264:14290–14297, 1989; Larsen et al., *Proc. Natl. Acad. Sci. USA* 86:8227–8231, 1989; Larsen et al., *J. Biol, Chem.* 265:7055–7061, 1990) and A and B transferases (Examples 4 and 7 above) (17 nucleotides out of 20 and 16 out of 20, respectively). However, degenerate oligos were used to increase the possibility of identifying something homologous to either sequence. The PCR product showed a major band of the expected size, indicating that the condition was stringent enough. After cloning and transformation, 89 out of 99 independent clones (numbers 1–89 in Table 9) were found to contain a fragment of the expected size, and were analyzed by DNA sequencing of the insert. They were categorized based on nucleotide sequence (Table 9).

TABLE 9

| Group | Classification of Clones Based on Nucleotide Sequence<br>Names of Clones |
|---|---|
| 1 | 1, 3, 5, 6, 7, 8, 17, 18, 22, 24, 27, 32, 34, 37, 38, 45, 49, 51, 56, 57, 59, 60, 66, 67, 69, 70, 75, 76, 77, 81, 83, 86, 87, 88 |
| 2 | 4, 10, 14, 39, 53, 62, 64, 68, 82, 89 |
| 3 | 2, 9, 15, 19, 28, 30, 31, 46, 48, 63, 72 |
| 4 | 13, 23, 55, 65 |
| 5 | 33, 52, 80 |
| 6 | 29, 85 |

Independent clones: 11, 12, 16, 20, 35, 36, 40, 41, 42, 43, 44, 47, 50, 54, 58, 71, 73, 74, 78, 79, 84.
Clones which failed to be sequenced: 21, 25, 26, 61.

By comparing nucleotide sequence with those of corresponding regions of human α1→3 galactosyltransferase pseudogene (Larsen et al., *J. Biol. Chem.* 265:7055–7061, 1990) and O gene (FIG. 4), it was discovered that the biggest group, 1, represents α1→3 galactosyltransferase pseudogene and the second biggest group, 2, represents O allele at the ABO locus. Group 3 showed humology with neither group 1 nor 2. However, group 4 (termed hgt4 for human glycosyltransferase group 4) showed humology with both groups 1 and (especially) 2. All the other groups and independent clones except clones 43 and 58 showed no homology with group 1 or 2. Although clones 43 and 58 showed extensive sequence homology with group 1, this was not pursued further because these are independent clones and we could not discriminate between PCR artifacts and genuine differences. The nucleotide and deduced amino acid sequence of hgt4 is shown in FIG. 10. About 47% or 69% nucleotide sequence homology were calculated between hgt4 and hGal or A transferase, respectively. As the next step for excluding the possibility of PCR amplification artifact, these DNA inserts were used as probes for Southern hybridization of human genomic DNA. $^{32}$P PCR-labeled probes made with inserts from groups 1, 2 and 4 were found to hybridize with fragments of different size, indicating that they are different, and that sequence differences are not artifactual but reside in the genomic DNA. Therefore, a homologous sequence (hgt4) for glycosyltransferase is shown herein by use of two primers prepared from well-conserved separate sequences.

From the foregoing, it will be evident that, although specific embodiments of the invention have been described herein for purposes of illustration, various modifications may be made without deviating from the spirit and scope of the invention.

---

We claim:

1. An isolated DNA molecule encoding a human histo-blood group A glycosyltransferase.

2. The DNA molecule of claim 1 consisting of cDNA.

3. The DNA molecule of claim 1 consisting of isolated genomic DNA.

4. An isolated DNA molecule encoding a human histo-blood group A glycosyltransferase wherein said glycosyltransferase consists of the amino acid sequence of FIG. 3 from alanine, amino acid 54, to proline, amino acid 353.

5. An isolated DNA molecule encoding a human histo-blood group A glycosyltransferase wherein said DNA molecule consists of a sequence of nucleotides as shown in FIG. 3 from nucleotide 160 to nucleotide 1059.

6. An isolated DNA molecule encoding a human histo-blood group A glycosyltransferase wherein said glycosyltransferase consists of the amino acid sequence of FIG. 3 from methionine, amino acid 1, to proline, amino acid 353.

7. An isolated DNA molecule encoding a human histo-blood group A glycosyltransferase wherein said DNA molecule consists of a sequence of nucleotides as shown in FIG. 3 from nucleotide 1 to nucleotide 1059.

8. An isolated DNA molecule encoding a human histo-blood group B glycosyltransferase.

9. The DNA molecule of claim 8 consisting of cDNA.

10. The DNA molecule of claim 8 consisting of isolated genomic DNA.

11. An isolated DNA molecule consisting of the nucleotide sequence of the human histo-blood group O glycosyltransferase gene.

12. The DNA molecule of claim 11 consisting of cDNA.

13. The DNA molecule of claim 11 consisting of isolated genomic DNA.

14. A DNA construct comprising a DNA sequence encoding a protein having the activity of a human histo-blood group A glycosyltransferase.

15. The DNA construct of claim 14 wherein at least a portion of the DNA sequence is a cDNA clone portion encoding a protein having the activity of histo-blood group A glycosyltransferase.

16. The DNA construct of claim 14 wherein at least a portion of the DNA sequence is a genomic clone portion encoding a protein having the activity of histo-blood group A glycosyltransferase.

17. A recombinant plasmid comprising a DNA sequence encoding human histo-blood group A glycosyltransferase.

18. The recombinant plasmid of claim 17 wherein the DNA sequence consists of histo-blood group A glycosyltransferase cDNA.

19. The recombinant plasmid of claim 17 wherein the DNA sequence consists of an isolated histo-blood group A glycosyltransferase genomic DNA sequence.

20. A recombinant plasmid which expresses histo-blood group A glycosyltransferase, said plasmid comprising a promoter followed downstream by a DNA sequence encoding human histo-blood group A glycosyltransferase, said DNA sequence being followed downstream by a polyadenylation signal.

21. Cells stably transfected with a recombinant plasmid comprising a DNA sequence a sequence encoding human histo-blood group A glycosyltransferase, said cells producing said glycosyltransferase in recoverable amounts.

22. A DNA construct comprising a DNA sequence encoding a protein having the activity of a human histo-blood group B glycosyltransferase.

23. The DNA construct of claim 22 wherein at least a portion of the DNA sequence is a cDNA clone portion encoding a protein having activity of histo-blood group B glycosyltransferase.

24. The DNA construct of claim 22 wherein at least a portion of the DNA sequence is a genomic clone portion encoding a protein having the activity of histo-blood group B glycosyltransferase.

25. A recombinant plasmid comprising a DNA sequence encoding human histo-blood group B glycosyltransferase.

26. The recombinant plasmid of claim 25 wherein the DNA sequence consists of histo-blood group B glycosyltransferase cDNA.

27. The recombinant plasmid of claim 25 wherein the DNA sequence consists of histo-blood group B glycosyltransferase genomic DNA.

28. A recombinant plasmid which expresses histo-blood group B glycosyltransferase, said plasmid comprising a promoter followed downstream by a DNA sequence encoding human histo-blood group B glycosyltransferase, said DNA sequence being followed downstream by a polyadenylation signal.

29. Cells stably transfected with a recombinant plasmid comprising a DNA sequence encoding human histo-blood group B glycosyltransferase, said cells producing said glycosyltransferase in recoverable amounts.

30. A DNA construct comprising a DNA sequence encoding a protein having the activity of a human histo-blood group A glycosyltransferase and the activity of a human histo-blood group B glycosyltransferase.

* * * * *

UNITED STATES PATENT AND TRADEMARK OFFICE
CERTIFICATE OF CORRECTION

PATENT NO. : 5,326,857
DATED : July 5, 1994
INVENTOR(S) : Fumi-ichiro Yamamoto et al.

It is certified that error appears in the above-indentified patent and that said Letters Patent is hereby corrected as shown below:

In column 90, claim 21, line 29, after "DNA sequence" and before "encoding", please delete "a sequence".

In column 90, claim 23, line 38, after "having" and before "activity", please insert --the--.

Signed and Sealed this

Fifteenth Day of November, 1994

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 69

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
    ( A ) NAME/KEY: Region
    ( B ) LOCATION: 21
    ( D ) OTHER INFORMATION: /label=unsure
        / note="This amino acid is unknown."

( x i ) SEQUENCE DESCRIPTION: SEQ ID NO:1:

```
Ala  Val  Arg  Glu  Pro  Asp  His  Leu  Gln  Arg  Val  Ser  Leu  Pro  Arg  Met
1                 5                            10                           15

Val  Tyr  Pro  Gln  Xaa  Lys  Val  Leu
               20
```

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Region
        ( B ) LOCATION: 6
        ( D ) OTHER INFORMATION: /label=unsure
            / note="This amino acid is unknown."

( x i ) SEQUENCE DESCRIPTION: SEQ ID NO:2:

```
Val  Leu  Thr  Pro  Gln  Xaa  Lys
1                   5
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:3:

```
Tyr  Leu  Leu  Arg  His  Lys  Pro  Thr  Lys
1                   5
```

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

```
Leu Arg Phe Thr Ala Val Pro Lys
1               5
```

( 2 ) INFORMATION FOR SEQ ID NO:5:

( i ) SEQUENCE CHARACTERISTICS:
  ( A ) LENGTH: 22 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
  ( A ) NAME/KEY: Region
  ( B ) LOCATION: 21
  ( D ) OTHER INFORMATION: /label=unsure
   / note="This amino acid is unknown."

( x i ) SEQUENCE DESCRIPTION: SEQ ID NO:5:

```
Ala Val Arg Glu Pro Asp His Leu Gln Arg Val Ser Leu Pro Arg Met
1               5                   10                  15
Val Tyr Pro Gln Xaa Lys
            20
```

( 2 ) INFORMATION FOR SEQ ID NO:6:

( i ) SEQUENCE CHARACTERISTICS:
  ( A ) LENGTH: 25 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
  ( A ) NAME/KEY: Region
  ( B ) LOCATION: 15..16
  ( D ) OTHER INFORMATION: /label=unsure
   / note="These amino acids are unknown."

( x i ) SEQUENCE DESCRIPTION: SEQ ID NO:6:

```
Asp Phe Met Val Gly His Arg Val His Tyr Tyr Val Phe Thr Xaa Xaa
1               5                   10                  15
Pro Ala Ala Val Pro Arg Val Thr Leu
            20                  25
```

( 2 ) INFORMATION FOR SEQ ID NO:7:

( i ) SEQUENCE CHARACTERISTICS:
  ( A ) LENGTH: 21 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
    ( A ) NAME/KEY: Region
    ( B ) LOCATION: 11
    ( D ) OTHER INFORMATION: /label=unsure
        / note="This amino acid is unknown."

( i x ) FEATURE:
    ( A ) NAME/KEY: Region
    ( B ) LOCATION: 20
    ( D ) OTHER INFORMATION: /label=unsure
        / note="This amino acid is unknown."

( x i ) SEQUENCE DESCRIPTION: SEQ ID NO:7:

```
Val Leu Ser Pro Glu Tyr Leu Trp Asp Gln Xaa Leu Leu Gly Trp Pro
 1               5                  10                  15

Ala Val Leu Xaa Lys
            20
```

( 2 ) INFORMATION FOR SEQ ID NO:8:

( i ) SEQUENCE CHARACTERISTICS:
    ( A ) LENGTH: 42 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
    ( A ) NAME/KEY: Region
    ( B ) LOCATION: 28
    ( D ) OTHER INFORMATION: /label=unsure
        / note="This amino acid is unknown."

( x i ) SEQUENCE DESCRIPTION: SEQ ID NO:8:

```
Asp Glu Gly His Phe Tyr Tyr Leu Gly Gly Phe Phe Gly Gly Ser Val
 1               5                  10                  15

Gln Glu Val Gln Arg Leu Thr Arg Ala Gln Cys Xaa Gln Ala Met Met
            20                  25                  30

Val Asp Gln Ala Asn Gly Ile Glu Ala Val
            35                  40
```

( 2 ) INFORMATION FOR SEQ ID NO:9:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:9:

```
Arg Val Leu Val Val Thr
 1               5
```

( 2 ) INFORMATION FOR SEQ ID NO:10:

( i ) SEQUENCE CHARACTERISTICS:
      ( A ) LENGTH: 40 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:10:

```
Val Tyr Pro Gln Pro Lys Val Leu Thr Pro Cys Arg Lys Asp Val Leu
 1               5                  10                  15

Val Val Thr Pro Trp Leu Ala Pro Ile Val Trp Glu Gly Thr Phe Asn
                20                  25                  30

Ile Asp Ile Leu Asn Glu Gly Phe
                35                  40
```

( 2 ) INFORMATION FOR SEQ ID NO:11:

( i ) SEQUENCE CHARACTERISTICS:
      ( A ) LENGTH: 30 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
      ( A ) NAME/KEY: Region
      ( B ) LOCATION: 24
      ( D ) OTHER INFORMATION: /label=unsure
             / note="This amino acid is unknown."

( i x ) FEATURE:
      ( A ) NAME/KEY: Region
      ( B ) LOCATION: 26..27
      ( D ) OTHER INFORMATION: /label=unsure
             / note="These amino acids are unknown."

( x i ) SEQUENCE DESCRIPTION: SEQ ID NO:11:

```
Glu Phe Arg Asp His Val Gly Val Glu Ile Leu Thr Pro Leu Phe Gly
 1               5                  10                  15

Thr Leu His Pro Gly Phe Tyr Xaa Glu Xaa Xaa Glu Ala Phe
                20                  25                  30
```

( 2 ) INFORMATION FOR SEQ ID NO:12:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:12:

```
Val Asp Gln Ala Asn Gly Ile Glu Ala Val
1               5                   10
```

( 2 ) INFORMATION FOR SEQ ID NO:13:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:13:

```
Val Gly His Arg Val His Tyr Tyr Val Phe Thr Asp Gln Pro Ala Ala
1               5                   10                  15

Val Pro Arg Val Thr Leu Gly Thr Gly Arg Gln Leu Ser Val Leu Glu
                20                  25                  30

Val Arg Ala Tyr Tyr
            35
```

( 2 ) INFORMATION FOR SEQ ID NO:14:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:14:

```
Ile Ser Asp Phe Cys Glu Arg Arg Phe Leu Ser Glu Val Asp Val Leu
1               5                   10                  15

Val Cys Val Asp
                20
```

( 2 ) INFORMATION FOR SEQ ID NO:15:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:15:

```
Ala Val Arg Glu Pro Asp His Leu Gln Arg Val Ser Leu Pro Arg Met
1               5                   10                  15
```

( 2 ) INFORMATION FOR SEQ ID NO:16:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:16:

```
Ala Val Arg Glu Pro Asp His Leu Gln Arg Val Ser Leu Pro Arg Met
 1               5                  10                  15
Val Tyr Pro Gln Pro Lys Val Leu Thr Pro Cys Arg Lys Asp Val Leu
            20                  25                  30
Val Val Thr Pro Trp Leu Ala Pro Ile Val Trp Glu Gly Thr Phe Asn
        35                  40                  45
Ile Asp Ile Leu Asn Glu Gly Phe
        50              55
```

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:17:

CCCGAAAGAA CCCCCCA                                                    18

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:18:

CCCGAAGAAC GCCCCCA                                                    17

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:19:

CGTTCTGCTA AAACCAAG  18

( 2 ) INFORMATION FOR SEQ ID NO:20:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:20:

GAAATCGCCC TCGTCCTT  18

( 2 ) INFORMATION FOR SEQ ID NO:21:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:21:

GGATCCAGGG GTGCACGGCC GGCGGC  26

( 2 ) INFORMATION FOR SEQ ID NO:22:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:22:

TGCTGGAGGT GCGCGCCTAC  20

( 2 ) INFORMATION FOR SEQ ID NO:23:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear (i i) MOLECULE TYPE: cDNA (i i i) HYPOTHETICAL: NO (i v) ANTI-SENSE: NO (v) FRAGMENT TYPE: N-terminal (x i) SEQUENCE DESCRIPTION: SEQ ID NO:23:

CGGAATTCGA GACCAGACCG GAGCC 25

(2) INFORMATION FOR SEQ ID NO:24:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (v) FRAGMENT TYPE: N-terminal (x i) SEQUENCE DESCRIPTION: SEQ ID NO:24:

CCTGAACTGC TCGTTGA 17

(2) INFORMATION FOR SEQ ID NO:25:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (v) FRAGMENT TYPE: N-terminal (x i) SEQUENCE DESCRIPTION: SEQ ID NO:25:

TGCCAGCTCC ATGTGACCGC 20

(2) INFORMATION FOR SEQ ID NO:26:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (v) FRAGMENT TYPE: N-terminal (x i) SEQUENCE DESCRIPTION: SEQ ID NO:26:

GAGCTCAGTA AGATGCT 17

(2) INFORMATION FOR SEQ ID NO:27:

(i) SEQUENCE CHARACTERISTICS:
(A) LENGTH: 20 base pairs
(B) TYPE: nucleic acid (C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: N-terminal (xi) SEQUENCE DESCRIPTION: SEQ ID NO:27:

GCGGCTCCCC CAGCCCCCGT  20

(2) INFORMATION FOR SEQ ID NO:28:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: N-terminal (xi) SEQUENCE DESCRIPTION: SEQ ID NO:28:

GAAATCGCCC TCGTCCTT  18

(2) INFORMATION FOR SEQ ID NO:29:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: N-terminal (xi) SEQUENCE DESCRIPTION: SEQ ID NO:29:

TGCTGGAGGT GCGCGCCTAC  20

(2) INFORMATION FOR SEQ ID NO:30:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: N-terminal (xi) SEQUENCE DESCRIPTION: SEQ ID NO:30:

CCGGATCCGT GTGATTTGAG GTGGGGAC  28

(2) INFORMATION FOR SEQ ID NO:31:

(i) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: N-terminal (xi) SEQUENCE DESCRIPTION: SEQ ID NO:31:

TACTACCTGG GGGGGTTCTT                                                                20

(2) INFORMATION FOR SEQ ID NO:32:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE: N-terminal (xi) SEQUENCE DESCRIPTION: SEQ ID NO:32:

CGGAATTCAW GYACTTCATG GTKGGCCA                                                       28

(2) INFORMATION FOR SEQ ID NO:33:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE: N-terminal (xi) SEQUENCE DESCRIPTION: SEQ ID NO:33:

CGGAATTCAG RTGGCTYTCR TCRTGCCA                                                       28

(2) INFORMATION FOR SEQ ID NO:34:

(i) SEQUENCE CHARACTERISTICS:
    (A) LENGTH: 1062 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE: N-terminal (ix) FEATURE:
    (A) NAME/KEY: CDS
    (B) LOCATION: 1..1059

(xi) SEQUENCE DESCRIPTION: SEQ ID NO:34:

```
ATG GCC GAG GTG TTG CGG ACG CTG GCC GGA AAA CCA AAA TGC CAC GCA        48
Met Ala Glu Val Leu Arg Thr Leu Ala Gly Lys Pro Lys Cys His Ala
 1           5                   10                  15

CTT CGA CCT ATG ATC CTT TTC CTA ATA ATG CTT GTC TTG GTC TTG TTT        96
Leu Arg Pro Met Ile Leu Phe Leu Ile Met Leu Val Leu Val Leu Phe
             20                  25                  30

GGT TAC GGG GTC CTA AGC CCC AGA AGT CTA ATG CCA GGA AGC CTG GAA       144
Gly Tyr Gly Val Leu Ser Pro Arg Ser Leu Met Pro Gly Ser Leu Glu
         35                  40                  45

CGG GGG TTC TGC ATG GCT GTT AGG GAA CCT GAC CAT CTG CAG CGC GTC       192
Arg Gly Phe Cys Met Ala Val Arg Glu Pro Asp His Leu Gln Arg Val
     50                  55                  60

TCG TTG CCA AGG ATG GTC TAC CCC CAG CCA AAG GTG CTG ACA CCG TGG       240
Ser Leu Pro Arg Met Val Tyr Pro Gln Pro Lys Val Leu Thr Pro Trp
 65                  70                  75                  80

AAG GAT GTC CTC GTG GTG ACC CCT TGG CTG GCT CCC ATT GTC TGG GAG       288
Lys Asp Val Leu Val Val Thr Pro Trp Leu Ala Pro Ile Val Trp Glu
                 85                  90                  95

GGC ACA TTC AAC ATC GAC ATC CTC AAC GAG CAG TTC AGG CTC CAG AAC       336
Gly Thr Phe Asn Ile Asp Ile Leu Asn Glu Gln Phe Arg Leu Gln Asn
         100                 105                 110

ACC ACC ATT GGG TTA ACT GTG TTT GCC ATC AAG AAA TAC GTG GCT TTC       384
Thr Thr Ile Gly Leu Thr Val Phe Ala Ile Lys Lys Tyr Val Ala Phe
     115                 120                 125

CTG AAG CTG TTC CTG GAG ACG GCG GAG AAG CAC TTC ATG GTG GGC CAC       432
Leu Lys Leu Phe Leu Glu Thr Ala Glu Lys His Phe Met Val Gly His
 130                 135                 140

CGT GTC CAC TAC TAT GTC TTC ACC GAC CAG CTG GCC GCG GTG CCC CGC       480
Arg Val His Tyr Tyr Val Phe Thr Asp Gln Leu Ala Ala Val Pro Arg
145                 150                 155                 160

GTG ACG CTG GGG ACC GGT CGG CAG CTG TCA GTG CTG GAG GTG CGC GCC       528
Val Thr Leu Gly Thr Gly Arg Gln Leu Ser Val Leu Glu Val Arg Ala
                 165                 170                 175

TAC AAG CGC TGG CAG GAC GTG TCC ATG CGC CGC ATG GAG ATG ATC AGT       576
Tyr Lys Arg Trp Gln Asp Val Ser Met Arg Arg Met Glu Met Ile Ser
         180                 185                 190

GAC TTC TGC GAG CGG CGC TTC CTC AGC GAG GTG GAT TAC CTG GTG TGC       624
Asp Phe Cys Glu Arg Arg Phe Leu Ser Glu Val Asp Tyr Leu Val Cys
     195                 200                 205

GTG GAC GTG GAC ATG GAG TTC CGC GAC CAC GTG GGC GTG GAG ATC CTG       672
Val Asp Val Asp Met Glu Phe Arg Asp His Val Gly Val Glu Ile Leu
 210                 215                 220

ACT CCG CTG TTC GGC ACC CTG CAC CCC GGC TTC TAC GGA AGC AGC CGG       720
Thr Pro Leu Phe Gly Thr Leu His Pro Gly Phe Tyr Gly Ser Ser Arg
225                 230                 235                 240

GAG GCC TTC ACC TAC GAG CGC CGG CCC CAG TCC CAG GCC TAC ATC CCC       768
Glu Ala Phe Thr Tyr Glu Arg Arg Pro Gln Ser Gln Ala Tyr Ile Pro
                 245                 250                 255

AAG GAC GAG GGC GAT TTC TAC TAC CTG GGG GGG TTC TTC GGG GGG TCG       816
Lys Asp Glu Gly Asp Phe Tyr Tyr Leu Gly Gly Phe Phe Gly Gly Ser
         260                 265                 270

GTG CAA GAG GTG CAG CGG CTC ACC AGG GCC TGC CAC CAG GCC ATG ATG       864
Val Gln Glu Val Gln Arg Leu Thr Arg Ala Cys His Gln Ala Met Met
     275                 280                 285

GTC GAC CAG GCC AAC GGC ATC GAG GCC GTG TGG CAC GAC GAG AGC CAC       912
Val Asp Gln Ala Asn Gly Ile Glu Ala Val Trp His Asp Glu Ser His
 290                 295                 300

CTG AAC AAG TAC CTG CTG CGC CAC AAA CCC ACC AAG GTG CTC TCC CCC       960
Leu Asn Lys Tyr Leu Leu Arg His Lys Pro Thr Lys Val Leu Ser Pro
305                 310                 315                 320

GAG TAC TTG TGG GAC CAG CAG CTG CTG GGC TGG CCC GCC GTC CTG AGG      1008
Glu Tyr Leu Trp Asp Gln Gln Leu Leu Gly Trp Pro Ala Val Leu Arg
```

|     |     |     |     |     | 325 |     |     |     |     | 330 |     |     |     |     | 335 |     |      |
|-----|-----|-----|-----|-----|-----|-----|-----|-----|-----|-----|-----|-----|-----|-----|-----|-----|------|
| AAG | CTG | AGG | TTC | ACT | GCG | GTG | CCC | AAG | AAC | CAC | CAG | GCG | GTC | CGG | AAC |     | 1056 |
| Lys | Leu | Arg | Phe | Thr | Ala | Val | Pro | Lys | Asn | His | Gln | Ala | Val | Arg | Asn |     |      |
|     |     |     | 340 |     |     |     |     | 345 |     |     |     |     | 350 |     |     |     |      |

| CCG | TGA | 1062 |
|-----|-----|------|
| Pro |     |      |

( 2 ) INFORMATION FOR SEQ ID NO:35:

( i ) SEQUENCE CHARACTERISTICS:
        ( A ) LENGTH: 353 amino acids
        ( B ) TYPE: amino acid
        ( D ) TOPOLOGY: linear ( i i ) MOLECULE TYPE: protein ( x i ) SEQUENCE DESCRIPTION: SEQ ID NO:35:

| Met | Ala | Glu | Val | Leu | Arg | Thr | Leu | Ala | Gly | Lys | Pro | Lys | Cys | His | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Arg | Pro | Met | Ile | Leu | Phe | Leu | Ile | Met | Leu | Val | Leu | Val | Leu | Phe |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Tyr | Gly | Val | Leu | Ser | Pro | Arg | Ser | Leu | Met | Pro | Gly | Ser | Leu | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Arg | Gly | Phe | Cys | Met | Ala | Val | Arg | Glu | Pro | Asp | His | Leu | Gln | Arg | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Leu | Pro | Arg | Met | Val | Tyr | Pro | Gln | Pro | Lys | Val | Leu | Thr | Pro | Trp |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Lys | Asp | Val | Leu | Val | Val | Thr | Pro | Trp | Leu | Ala | Pro | Ile | Val | Trp | Glu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Gly | Thr | Phe | Asn | Ile | Asp | Ile | Leu | Asn | Glu | Gln | Phe | Arg | Leu | Gln | Asn |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Thr | Thr | Ile | Gly | Leu | Thr | Val | Phe | Ala | Ile | Lys | Lys | Tyr | Val | Ala | Phe |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Leu | Lys | Leu | Phe | Leu | Glu | Thr | Ala | Glu | Lys | His | Phe | Met | Val | Gly | His |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Arg | Val | His | Tyr | Tyr | Val | Phe | Thr | Asp | Gln | Leu | Ala | Ala | Val | Pro | Arg |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Val | Thr | Leu | Gly | Thr | Gly | Arg | Gln | Leu | Ser | Val | Leu | Glu | Val | Arg | Ala |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Tyr | Lys | Arg | Trp | Gln | Asp | Val | Ser | Met | Arg | Arg | Met | Glu | Met | Ile | Ser |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Asp | Phe | Cys | Glu | Arg | Arg | Phe | Leu | Ser | Glu | Val | Asp | Tyr | Leu | Val | Cys |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Val | Asp | Val | Asp | Met | Glu | Phe | Arg | Asp | His | Val | Gly | Val | Glu | Ile | Leu |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Thr | Pro | Leu | Phe | Gly | Thr | Leu | His | Pro | Gly | Phe | Tyr | Gly | Ser | Ser | Arg |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Glu | Ala | Phe | Thr | Tyr | Glu | Arg | Arg | Pro | Gln | Ser | Gln | Ala | Tyr | Ile | Pro |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Lys | Asp | Glu | Gly | Asp | Phe | Tyr | Tyr | Leu | Gly | Gly | Phe | Phe | Gly | Gly | Ser |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Val | Gln | Glu | Val | Gln | Arg | Leu | Thr | Arg | Ala | Cys | His | Gln | Ala | Met | Met |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Val | Asp | Gln | Ala | Asn | Gly | Ile | Glu | Ala | Val | Trp | His | Asp | Glu | Ser | His |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Leu | Asn | Lys | Tyr | Leu | Leu | Arg | His | Lys | Pro | Thr | Lys | Val | Leu | Ser | Pro |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Glu | Tyr | Leu | Trp | Asp | Gln | Gln | Leu | Leu | Gly | Trp | Pro | Ala | Val | Leu | Arg |
|-----|-----|-----|-----|-----|-----|-----|-----|-----|-----|-----|-----|-----|-----|-----|-----|

|   | 325 | 330 | 335 |
|---|---|---|---|

Lys Leu Arg Phe Thr Ala Val Pro Lys Asn His Gln Ala Val Arg Asn
            340                 345                 350

Pro ( 2 ) INFORMATION FOR SEQ ID NO:36:

( i ) SEQUENCE CHARACTERISTICS:
         ( A ) LENGTH: 353 amino acids
         ( B ) TYPE: amino acid
         ( C ) STRANDEDNESS: single
         ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:36:

Met Ala Glu Val Leu Arg Thr Leu Ala Gly Lys Pro Lys Cys His Ala
 1               5                  10                  15

Leu Arg Pro Met Ile Leu Phe Leu Ile Met Leu Val Leu Val Leu Phe
            20                  25                  30

Gly Tyr Gly Val Leu Ser Pro Arg Ser Leu Met Pro Gly Ser Leu Glu
            35                  40                  45

Arg Gly Phe Cys Met Ala Val Arg Glu Pro Asp His Leu Gln Arg Val
        50                  55                  60

Ser Leu Pro Arg Met Val Tyr Pro Gln Pro Lys Val Leu Thr Pro Trp
65                  70                  75                  80

Lys Asp Val Leu Val Val Thr Pro Trp Leu Ala Pro Ile Val Trp Glu
                85                  90                  95

Gly Thr Phe Asn Ile Asp Ile Leu Asn Glu Gln Phe Arg Leu Gln Asn
                100                 105                 110

Thr Thr Ile Gly Leu Thr Val Phe Ala Ile Lys Lys Tyr Val Ala Phe
            115                 120                 125

Leu Lys Leu Phe Leu Glu Thr Ala Glu Lys His Phe Met Val Gly His
    130                 135                 140

Arg Val His Tyr Tyr Val Phe Thr Asp Gln Leu Ala Ala Val Pro Arg
145                 150                 155                 160

Val Thr Leu Gly Thr Gly Arg Gln Leu Ser Val Leu Glu Val Arg Ala
                165                 170                 175

Tyr Lys Arg Trp Gln Asp Val Ser Met Arg Arg Met Glu Met Ile Ser
            180                 185                 190

Asp Phe Cys Glu Arg Arg Phe Leu Ser Glu Val Asp Tyr Leu Val Cys
    195                 200                 205

Val Asp Val Asp Met Glu Phe Arg Asp His Val Gly Val Glu Ile Leu
210                 215                 220

Thr Pro Leu Phe Gly Thr Leu His Pro Gly Phe Tyr Gly Ser Ser Arg
225                 230                 235                 240

Glu Ala Phe Thr Glu Tyr Arg Arg Pro Gln Ser Gln Ala Tyr Ile Pro
                245                 250                 255

Lys Asp Glu Gly Asp Phe Tyr Tyr Leu Gly Gly Phe Phe Gly Gly Ser
            260                 265                 270

Val Gln Glu Val Gln Arg Leu Thr Arg Ala Cys His Gln Ala Met Met
    275                 280                 285

Val Asp Gln Ala Asn Gly Ile Glu Ala Val Trp His Asp Glu Ser His
290                 295                 300

(2) INFORMATION FOR SEQ ID NO:37:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (ix) FEATURE:
        (A) NAME/KEY: Region
        (B) LOCATION: 1..10
        (D) OTHER INFORMATION: /label=unsure
        / note="These amino acids are unknown."

(xi) SEQUENCE DESCRIPTION: SEQ ID NO:37:

```
Xaa Xaa Xaa Xaa Xaa Xaa Xaa Xaa Xaa Xaa Lys Pro Lys Cys His Ala
 1               5                  10                  15

Leu Arg Pro Met Ile Leu Phe Leu Ile Met Leu Val Leu Val Leu Phe
                20                  25                  30

Gly Tyr Gly Val Leu Ser Pro Arg Ser Leu Met Pro Gly Ser Leu Glu
            35                  40                  45

Arg Gly Phe Cys Met Ala Val Arg Glu Pro Asp His Leu Gln Arg Val
        50                  55                  60

Ser Leu Pro Arg Met Val Tyr Pro Gln Pro Lys Val Leu Thr Pro Cys
65                  70                  75                  80

Arg Lys Asp Val Leu Val Val Pro Leu Gly Trp Leu Pro Leu Ser Gly
                85                  90                  95

Arg Ala His Ser Thr Ser Thr Ser Ser Thr Ser Ser Ser Gly Ser Arg
            100                 105                 110

Thr Pro Pro Leu Gly
                115
```

(2) INFORMATION FOR SEQ ID NO:38:

(i) SEQUENCE CHARACTERISTICS:
        (A) LENGTH: 354 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:38:

```
Leu Asn Lys Tyr Leu Leu Arg His Lys Pro Thr Lys Val Leu Ser Pro
305                 310                 315                 320

Glu Tyr Leu Trp Asp Gln Gln Leu Leu Gly Trp Pro Ala Val Leu Arg
                325                 330                 335

Lys Leu Arg Phe Thr Ala Val Pro Lys Asn His Gln Ala Val Arg Asn
            340                 345                 350

Pro

Met Ala Glu Val Leu Arg Thr Leu Ala Gly Lys Pro Lys Cys His Ala
 1               5                  10                  15
```

Leu Arg Pro Met Ile Leu Phe Leu Ile Met Leu Val Leu Val Leu Phe
          20              25              30

Gly Tyr Gly Val Leu Ser Pro Arg Ser Leu Met Pro Gly Ser Leu Glu
         35              40              45

Arg Gly Phe Cys Met Ala Val Arg Glu Pro Asp His Leu Gln Arg Val
     50              55              60

Ser Leu Pro Arg Met Val Tyr Pro Gln Pro Lys Val Leu Thr Pro Cys
65              70              75              80

Arg Lys Asp Val Leu Val Val Thr Pro Trp Leu Ala Pro Ile Val Trp
             85              90              95

Glu Gly Thr Phe Asn Ile Asp Ile Leu Asn Glu Gln Phe Arg Leu Gln
             100             105             110

Asn Thr Thr Ile Gly Leu Thr Val Phe Ala Ile Lys Lys Tyr Val Ala
         115             120             125

Phe Leu Lys Leu Phe Leu Glu Thr Ala Glu Lys His Phe Met Val Gly
     130             135             140

His Arg Val His Tyr Tyr Val Phe Thr Asp Gln Pro Ala Ala Val Pro
145             150             155             160

Arg Val Thr Leu Gly Thr Gly Arg Gln Leu Ser Val Leu Glu Val Arg
             165             170             175

Ala Tyr Lys Arg Trp Gln Asp Val Ser Met Arg Arg Met Glu Met Ile
         180             185             190

Ser Asp Phe Cys Glu Arg Arg Phe Leu Ser Glu Val Asp Tyr Leu Val
     195             200             205

Cys Val Asp Val Asp Met Glu Phe Arg Asp His Val Gly Val Glu Ile
210             215             220

Leu Thr Pro Leu Phe Gly Thr Leu His Pro Gly Phe Tyr Gly Ser Ser
225             230             235             240

Arg Glu Ala Phe Thr Glu Tyr Arg Arg Pro Gln Ser Gln Ala Tyr Ile
             245             250             255

Pro Lys Asp Glu Gly Asp Phe Tyr Tyr Leu Gly Gly Phe Phe Gly Gly
         260             265             270

Ser Val Gln Glu Val Gln Arg Leu Thr Arg Ala Cys His Gln Ala Met
     275             280             285

Met Val Asp Gln Ala Asn Gly Ile Glu Ala Val Trp His Asp Glu Ser
290             295             300

His Leu Asn Lys Tyr Leu Leu Arg His Lys Pro Thr Lys Val Leu Ser
305             310             315             320

Pro Glu Tyr Leu Trp Asp Gln Gln Leu Leu Gly Trp Pro Ala Val Leu
             325             330             335

Arg Lys Leu Arg Phe Thr Ala Val Pro Lys Asn His Gln Ala Val Arg
             340             345             350

Asn Pro ( 2 ) INFORMATION FOR SEQ ID NO:39:

( i ) SEQUENCE CHARACTERISTICS:
      ( A ) LENGTH: 354 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:39:

```
Met Ala Glu Val Leu Arg Thr Leu Ala Gly Lys Pro Lys Cys His Ala
 1               5                  10                  15

Leu Arg Pro Met Ile Leu Phe Leu Ile Met Leu Val Leu Val Leu Phe
            20                  25                  30

Gly Tyr Gly Val Leu Ser Pro Arg Ser Leu Met Pro Gly Ser Leu Glu
        35                  40                  45

Arg Gly Phe Cys Met Ala Val Arg Glu Pro Asp His Leu Gln Arg Val
    50                  55                  60

Ser Leu Pro Arg Met Val Tyr Pro Gln Pro Lys Val Leu Thr Pro Cys
65                  70                  75                  80

Arg Lys Asp Val Leu Val Val Thr Pro Trp Leu Ala Pro Ile Val Trp
                85                  90                  95

Glu Gly Thr Phe Asn Ile Asp Ile Leu Asn Glu Gln Phe Arg Leu Gln
            100                 105                 110

Asn Thr Thr Ile Gly Leu Thr Val Phe Ala Ile Lys Lys Tyr Val Ala
        115                 120                 125

Phe Leu Lys Leu Phe Leu Glu Thr Ala Glu Lys His Phe Met Val Gly
    130                 135                 140

His Arg Val His Tyr Tyr Val Phe Thr Asp Gln Pro Ala Ala Val Pro
145                 150                 155                 160

Arg Val Thr Leu Gly Thr Gly Arg Gln Leu Ser Val Leu Glu Val Gly
                165                 170                 175

Ala Tyr Lys Arg Trp Gln Asp Val Ser Met Arg Arg Met Glu Met Ile
            180                 185                 190

Ser Asp Phe Cys Glu Arg Arg Phe Leu Ser Glu Val Asp Tyr Leu Val
        195                 200                 205

Cys Val Asp Val Asp Met Glu Phe Arg Asp His Val Gly Val Glu Ile
    210                 215                 220

Leu Thr Pro Leu Phe Gly Thr Leu His Pro Ser Phe Tyr Gly Ser Ser
225                 230                 235                 240

Arg Glu Ala Phe Thr Glu Tyr Arg Arg Pro Gln Ser Gln Ala Tyr Ile
                245                 250                 255

Pro Lys Asp Glu Gly Asp Phe Tyr Tyr Met Gly Ala Phe Phe Gly Gly
            260                 265                 270

Ser Val Gln Glu Val Gln Arg Leu Thr Arg Ala Cys His Gln Ala Met
        275                 280                 285

Met Val Asp Gln Ala Asn Gly Ile Glu Ala Val Trp His Asp Glu Ser
    290                 295                 300

His Leu Asn Lys Tyr Leu Leu Arg His Lys Pro Thr Lys Val Leu Ser
305                 310                 315                 320

Pro Glu Tyr Leu Trp Asp Gln Gln Leu Leu Gly Trp Pro Ala Val Leu
                325                 330                 335

Arg Lys Leu Arg Phe Thr Ala Val Pro Lys Asn His Gln Ala Val Arg
            340                 345                 350

Asn Pro
```

( 2 ) INFORMATION FOR SEQ ID NO:40:

( i ) SEQUENCE CHARACTERISTICS:
        ( A ) LENGTH: 117 amino acids
        ( B ) TYPE: amino acid
        ( C ) STRANDEDNESS: single
        ( D ) TOPOLOGY: linear ( i i ) MOLECULE TYPE: peptide -continued (iii) HYPOTHETICAL: NO (iv) ANTI-SENSE: NO (v) FRAGMENT TYPE: N-terminal (ix) FEATURE:
    (A) NAME/KEY: Region
    (B) LOCATION: 1
    (D) OTHER INFORMATION: /label=unsure
        / note="This amino acid is unknown."

(xi) SEQUENCE DESCRIPTION: SEQ ID NO:40:

```
Xaa Ala Glu Val Leu Arg Thr Leu Ala Gly Lys Pro Lys Cys His Ala
 1               5                  10                       15

Leu Arg Pro Met Ile Leu Phe Leu Ile Met Leu Val Leu Val Leu Phe
                20              25              30

Gly Tyr Gly Phe Leu Ser Pro Arg Ser Leu Met Pro Gly Ser Leu Glu
            35              40              45

Arg Gly Phe Cys Met Ala Val Arg Glu Pro Asp His Leu Gln His Val
        50              55              60

Ser Leu Pro Arg Met Val Tyr Pro Gln Ser Lys Val Leu Thr Pro Cys
65                  70              75                       80

Arg Lys Asp Val Leu Val Val Pro Leu Gly Trp Leu Pro Leu Ser Gly
                85              90              95

Arg Ala Arg Ser Thr Ser Thr Ser Ser Thr Ser Ser Ser Gly Ser Arg
            100             105             110

Thr Pro Pro Leu Gly
            115
```

(2) INFORMATION FOR SEQ ID NO:41:

(i) SEQUENCE CHARACTERISTICS:
    (A) LENGTH: 354 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:41:

```
Met Ala Glu Val Leu Arg Thr Leu Ala Gly Lys Pro Lys Cys His Ala
 1               5                  10                       15

Leu Arg Pro Met Ile Leu Phe Leu Ile Met Leu Val Leu Val Leu Phe
                20              25              30

Gly Tyr Gly Val Leu Ser Pro Arg Ser Leu Met Pro Gly Ser Leu Glu
            35              40              45

Arg Gly Phe Cys Met Ala Val Arg Glu Pro Asp His Leu Gln Arg Val
        50              55              60

Ser Leu Pro Arg Met Val Tyr Pro Gln Pro Lys Val Leu Thr Pro Cys
65                  70              75                       80

Arg Lys Asp Val Leu Val Val Thr Pro Trp Leu Ala Pro Ile Val Trp
                85              90              95

Glu Gly Thr Phe Asn Ile Asp Ile Leu Asn Glu Gln Phe Arg Leu Gln
            100             105             110

Asn Thr Thr Ile Gly Leu Thr Val Phe Ala Ile Lys Lys Tyr Val Ala
        115             120             125

Phe Leu Lys Leu Phe Leu Glu Thr Ala Glu Lys His Phe Met Val Gly
```

|     |     |     | 130 |     |     |     | 135 |     |     |     | 140 |     |     |     |
|-----|-----|-----|-----|-----|-----|-----|-----|-----|-----|-----|-----|-----|-----|-----|
| His | Arg | Val | His | Tyr | Tyr | Val | Phe | Thr | Asp | Gln | Pro | Ala | Ala | Val | Pro |
| 145 |     |     |     |     | 150 |     |     |     | 155 |     |     |     |     | 160 |
| Arg | Val | Thr | Leu | Gly | Thr | Gly | Arg | Gln | Leu | Ser | Val | Leu | Glu | Val | Gly |
|     |     |     |     | 165 |     |     |     | 170 |     |     |     |     | 175 |     |
| Ala | Tyr | Lys | Arg | Trp | Gln | Asp | Val | Ser | Met | Arg | Arg | Met | Glu | Met | Ile |
|     |     |     | 180 |     |     |     |     | 185 |     |     |     |     | 190 |     |
| Ser | Asp | Phe | Cys | Glu | Arg | Arg | Phe | Leu | Ser | Glu | Val | Asp | Tyr | Leu | Val |
|     |     | 195 |     |     |     | 200 |     |     |     |     |     | 205 |     |     |
| Cys | Val | Asp | Val | Asp | Met | Glu | Phe | Arg | Asp | His | Val | Gly | Val | Glu | Ile |
|     | 210 |     |     |     |     | 215 |     |     |     |     | 220 |     |     |     |
| Leu | Thr | Pro | Leu | Phe | Gly | Thr | Leu | His | Pro | Ser | Phe | Tyr | Gly | Ser | Ser |
| 225 |     |     |     |     | 230 |     |     |     |     | 235 |     |     |     |     | 240 |
| Arg | Glu | Ala | Phe | Thr | Glu | Tyr | Arg | Arg | Pro | Gln | Ser | Gln | Ala | Tyr | Ile |
|     |     |     |     | 245 |     |     |     |     | 250 |     |     |     |     | 255 |     |
| Pro | Lys | Asp | Glu | Gly | Asp | Phe | Tyr | Tyr | Met | Gly | Ala | Phe | Phe | Gly | Gly |
|     |     |     |     | 260 |     |     |     | 265 |     |     |     |     | 270 |     |
| Ser | Val | Gln | Glu | Val | Gln | Arg | Leu | Thr | Arg | Ala | Cys | His | Gln | Ala | Met |
|     |     | 275 |     |     |     |     | 280 |     |     |     |     | 285 |     |     |
| Met | Val | Asp | Gln | Ala | Asn | Gly | Ile | Glu | Ala | Val | Trp | His | Asp | Glu | Ser |
|     | 290 |     |     |     |     | 295 |     |     |     |     | 300 |     |     |     |
| His | Leu | Asn | Lys | Tyr | Leu | Leu | Arg | His | Lys | Pro | Thr | Lys | Val | Leu | Ser |
| 305 |     |     |     |     | 310 |     |     |     |     | 315 |     |     |     |     | 320 |
| Pro | Glu | Tyr | Leu | Trp | Asp | Gln | Gln | Leu | Leu | Gly | Trp | Pro | Ala | Val | Leu |
|     |     |     |     | 325 |     |     |     |     | 330 |     |     |     |     | 335 |     |
| Arg | Lys | Leu | Arg | Phe | Thr | Ala | Val | Pro | Lys | Asn | His | Gln | Ala | Val | Arg |
|     |     |     | 340 |     |     |     |     | 345 |     |     |     |     | 350 |     |
| Asn | Pro |     |     |     |     |     |     |     |     |     |     |     |     |     |     |

( 2 ) INFORMATION FOR SEQ ID NO:42:

( i ) SEQUENCE CHARACTERISTICS:
        ( A ) LENGTH: 117 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Region
        ( B ) LOCATION: 1
        ( D ) OTHER INFORMATION: /label=unsure
            / note="This amino acid is unknown."

( x i ) SEQUENCE DESCRIPTION: SEQ ID NO:42:

| Xaa | Ala | Glu | Val | Leu | Arg | Thr | Leu | Ala | Gly | Lys | Pro | Lys | Cys | His | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Leu | Arg | Pro | Met | Ile | Leu | Phe | Leu | Ile | Met | Leu | Val | Leu | Val | Leu | Phe |
|     |     |     | 20  |     |     |     |     | 25  |     |     |     |     | 30  |     |     |
| Gly | Tyr | Gly | Val | Leu | Ser | Pro | Arg | Ser | Leu | Met | Pro | Gly | Ser | Leu | Glu |
|     |     | 35  |     |     |     |     | 40  |     |     |     |     | 45  |     |     |     |
| Arg | Gly | Phe | Cys | Met | Ala | Val | Arg | Glu | Pro | Asp | His | Leu | Gln | Arg | Val |
|     | 50  |     |     |     |     | 55  |     |     |     |     | 60  |     |     |     |     |
| Ser | Leu | Pro | Arg | Met | Val | Tyr | Pro | Gln | Pro | Lys | Val | Leu | Thr | Pro | Cys |
| 65  |     |     |     |     | 70  |     |     |     |     | 75  |     |     |     |     | 80  |

```
     Arg Lys Asp Val Leu Val Val Pro Leu Gly Trp Leu Pro Leu Ser Gly
                     85              90                  95
     Arg Ala His Ser Thr Ser Thr Ser Ser Thr Ser Ser Ser Gly Ser Arg
                 100             105             110
     Thr Pro Pro Leu Gly
                 115
```

( 2 ) INFORMATION FOR SEQ ID NO:43:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:43:

CGTGGTGACC CCTT                                                              14

( 2 ) INFORMATION FOR SEQ ID NO:44:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:44:

CGTGGTACCC CTT                                                               13

( 2 ) INFORMATION FOR SEQ ID NO:45:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:45:

GAGGTGCGCG CCT                                                               13

( 2 ) INFORMATION FOR SEQ ID NO:46:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:46:

GAGGTGGGCG CCT    13

( 2 ) INFORMATION FOR SEQ ID NO:47:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:47:

CACCCCGGCT TCT    13

( 2 ) INFORMATION FOR SEQ ID NO:48:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:48:

CACCCCAGCT TCT    13

( 2 ) INFORMATION FOR SEQ ID NO:49:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:49:

TACTACCTGG GGGGGTTCTT    20

( 2 ) INFORMATION FOR SEQ ID NO:50:

( i ) SEQUENCE CHARACTERISTICS:
( A ) LENGTH: 20 base pairs
( B ) TYPE: nucleic acid
( C ) STRANDEDNESS: single ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:50:

TACTACATGG GGGCGTTCTT 20

( 2 ) INFORMATION FOR SEQ ID NO:51:

( i ) SEQUENCE CHARACTERISTICS:
      ( A ) LENGTH: 354 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:51:

```
Met Ala Glu Val Leu Arg Thr Leu Ala Gly Lys Pro Lys Cys His Ala
 1               5                  10                  15

Leu Arg Pro Met Ile Leu Phe Leu Ile Met Leu Val Leu Val Leu Phe
                20                  25                  30

Gly Tyr Gly Val Leu Ser Pro Arg Ser Leu Met Pro Gly Ser Leu Glu
            35                  40                  45

Arg Gly Phe Cys Met Ala Val Arg Glu Pro Asp His Leu Gln Arg Val
        50                  55                  60

Ser Leu Pro Arg Met Val Tyr Pro Gln Pro Lys Val Leu Thr Pro Cys
65                  70                  75                  80

Arg Lys Asp Val Leu Val Val Thr Pro Trp Leu Ala Pro Ile Val Trp
                85                  90                  95

Glu Gly Thr Phe Asn Ile Asp Ile Leu Asn Glu Gln Phe Arg Leu Gln
                100                 105                 110

Asn Thr Thr Ile Gly Leu Thr Val Phe Ala Ile Lys Lys Tyr Val Ala
            115                 120                 125

Phe Leu Lys Leu Phe Leu Glu Thr Ala Glu Lys His Phe Met Val Gly
        130                 135                 140

His Arg Val His Tyr Tyr Val Phe Thr Asp Gln Pro Ala Ala Val Pro
145                 150                 155                 160

Arg Val Thr Leu Gly Thr Gly Arg Gln Leu Ser Val Leu Glu Val Arg
                165                 170                 175

Ala Tyr Lys Arg Trp Gln Asp Val Ser Met Arg Arg Met Glu Met Ile
                180                 185                 190

Ser Asp Phe Cys Glu Arg Arg Phe Leu Ser Glu Val Asp Tyr Leu Val
            195                 200                 205

Cys Val Asp Val Asp Met Glu Phe Arg Asp His Val Gly Val Glu Ile
        210                 215                 220

Leu Thr Pro Leu Phe Gly Thr Leu His Pro Gly Phe Tyr Gly Ser Ser
225                 230                 235                 240

Arg Glu Ala Phe Thr Tyr Glu Arg Arg Pro Gln Ser Gln Ala Tyr Ile
                245                 250                 255

Pro Lys Asp Glu Gly Asp Phe Tyr Tyr Leu Gly Gly Phe Phe Gly Gly
```

|   |   |   |   |   | 260 |   |   |   |   | 265 |   |   |   |   | 270 |   |
|---|---|---|---|---|---|---|---|---|---|---|---|---|---|---|---|---|
| Ser | Val | Gln | Glu | Val | Gln | Arg | Leu | Thr | Arg | Ala | Cys | His | Gln | Ala | Met |   |
|   |   | 275 |   |   |   |   | 280 |   |   |   |   | 285 |   |   |   |   |
| Met | Val | Asp | Gln | Ala | Asn | Gly | Ile | Glu | Ala | Val | Trp | His | Asp | Glu | Ser |   |
|   |   | 290 |   |   |   |   | 295 |   |   |   |   | 300 |   |   |   |   |
| His | Leu | Asn | Lys | Tyr | Leu | Leu | Arg | His | Lys | Pro | Thr | Lys | Val | Leu | Ser |   |
| 305 |   |   |   |   | 310 |   |   |   |   | 315 |   |   |   |   | 320 |   |
| Pro | Glu | Tyr | Leu | Trp | Asp | Gln | Gln | Leu | Leu | Gly | Trp | Pro | Ala | Val | Leu |   |
|   |   |   |   | 325 |   |   |   |   | 330 |   |   |   |   | 335 |   |   |
| Arg | Lys | Leu | Arg | Phe | Thr | Ala | Val | Pro | Lys | Asn | His | Gln | Ala | Val | Arg |   |
|   |   |   | 340 |   |   |   |   | 345 |   |   |   |   | 350 |   |   |   |
| Asn | Pro |   |   |   |   |   |   |   |   |   |   |   |   |   |   |   |

(2) INFORMATION FOR SEQ ID NO:52:

( i ) SEQUENCE CHARACTERISTICS:
        ( A ) LENGTH: 375 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Region
        ( B ) LOCATION: 1..53
        ( D ) OTHER INFORMATION: /label=unsure
            / note="These amino acids are unknown."

( x i ) SEQUENCE DESCRIPTION: SEQ ID NO:52:

|   |   |   |   |   |   |   |   |   |   |   |   |   |   |   |   |
|---|---|---|---|---|---|---|---|---|---|---|---|---|---|---|---|
| Xaa | Xaa | Xaa | Xaa | Xaa | Xaa | Xaa | Xaa | Xaa | Xaa | Xaa | Xaa | Xaa | Xaa | Xaa | Xaa |
| 1 |   |   |   | 5 |   |   |   |   | 10 |   |   |   |   | 15 |   |
| Xaa | Xaa | Xaa | Xaa | Xaa | Xaa | Xaa | Xaa | Xaa | Xaa | Xaa | Xaa | Xaa | Xaa | Xaa | Xaa |
|   |   |   | 20 |   |   |   |   | 25 |   |   |   |   | 30 |   |   |
| Xaa | Xaa | Xaa | Xaa | Xaa | Xaa | Xaa | Xaa | Xaa | Xaa | Xaa | Xaa | Xaa | Xaa | Xaa | Xaa |
|   |   | 35 |   |   |   |   | 40 |   |   |   |   | 45 |   |   |   |
| Xaa | Xaa | Xaa | Xaa | Xaa | Ala | Val | Arg | Glu | Pro | Asp | His | Leu | Gln | Arg | Val |
|   | 50 |   |   |   |   | 55 |   |   |   |   | 60 |   |   |   |   |
| Ser | Leu | Pro | Arg | Met | Val | Tyr | Pro | Gln | Pro | Lys | Val | Leu | Thr | Pro | Cys |
| 65 |   |   |   |   | 70 |   |   |   |   | 75 |   |   |   |   | 80 |
| Arg | Lys | Asp | Val | Leu | Val | Val | Thr | Pro | Trp | Leu | Ala | Pro | Ile | Val | Trp |
|   |   |   |   | 85 |   |   |   |   | 90 |   |   |   |   | 95 |   |
| Glu | Gly | Thr | Phe | Asn | Ile | Asp | Ile | Leu | Asn | Glu | Gln | Phe | Arg | Leu | Gln |
|   |   |   | 100 |   |   |   |   | 105 |   |   |   |   | 110 |   |   |
| Asn | Thr | Thr | Ile | Gly | Leu | Thr | Val | Phe | Ala | Ile | Lys | Lys | Tyr | Val | Ala |
|   |   | 115 |   |   |   |   | 120 |   |   |   |   | 125 |   |   |   |
| Phe | Leu | Lys | Leu | Phe | Leu | Glu | Thr | Ala | Glu | Lys | His | Phe | Met | Val | Gly |
|   | 130 |   |   |   |   | 135 |   |   |   |   | 140 |   |   |   |   |
| His | Arg | Val | His | Tyr | Tyr | Val | Phe | Thr | Asp | Gln | Leu | Ala | Ala | Val | Pro |
| 145 |   |   |   |   | 150 |   |   |   |   | 155 |   |   |   |   | 160 |
| Arg | Val | Thr | Leu | Gly | Thr | Gly | Arg | Gln | Leu | Ser | Val | Leu | Glu | Val | Arg |
|   |   |   |   | 165 |   |   |   |   | 170 |   |   |   |   | 175 |   |
| Ala | Tyr | Lys | Arg | Trp | Gln | Asp | Val | Ser | Met | Arg | Arg | Met | Glu | Met | Ile |
|   |   |   | 180 |   |   |   |   | 185 |   |   |   |   | 190 |   |   |
| Ser | Asp | Phe | Cys | Glu | Arg | Arg | Phe | Leu | Ser | Glu | Val | Asp | Tyr | Leu | Val |
|   |   | 195 |   |   |   |   | 200 |   |   |   |   | 205 |   |   |   |

|  |  |  |  |  |  |  |  |  |  |  |  |  |  |  |
|---|---|---|---|---|---|---|---|---|---|---|---|---|---|---|
| Cys | Val 210 | Asp | Val | Asp | Met 215 | Glu | Phe | Arg | Asp | His 220 | Val | Gly | Val | Glu | Ile |
| Leu 225 | Thr | Pro | Leu | Phe | Gly 230 | Thr | Leu | His | Pro | Gly 235 | Phe | Tyr | Gly | Ser | Ser 240 |
| Arg | Glu | Ala | Phe | Thr 245 | Tyr | Glu | Arg | Arg | Pro 250 | Gln | Ser | Gln | Ala | Tyr 255 | Ile |
| Pro | Lys | Asp | Glu 260 | Gly | Asp | Phe | Tyr | Tyr 265 | Leu | Gly | Gly | Phe | Phe 270 | Gly | Gly |
| Ser | Val | Gln 275 | Glu | Val | Gln | Arg | Leu 280 | Thr | Arg | Ala | Cys | His 285 | Gln | Ala | Met |
| Met | Val 290 | Asp | Gln | Ala | Asn | Gly 295 | Ile | Glu | Ala | Val | Trp 300 | His | Asp | Glu | Ser |
| His 305 | Leu | Asn | Lys | Tyr | Leu 310 | Leu | Arg | His | Lys | Pro 315 | Thr | Lys | Val | Leu | Ser 320 |
| Pro | Glu | Tyr | Leu | Trp | Asp 325 | Gln | Gln | Leu | Leu 330 | Gly | Trp | Pro | Ala 335 | Val | Leu |
| Arg | Lys | Leu | Arg 340 | Phe | Thr | Ala | Val | Pro 345 | Lys | Asn | His | Gln | Ala 350 | Val | Arg |
| Asn | Arg | Glu 355 | Arg | Leu | Pro | Gly | Ala 360 | Leu | Gly | Gly | Leu | Pro 365 | Ala | Ala | Pro |
| Ser | Pro 370 | Ser | Arg | Pro | Trp | Phe 375 | | | | | | | | | |

( 2 ) INFORMATION FOR SEQ ID NO:53:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:53:

| AACCACCAGG | CGGTCCGGAA | CCCGTGAGCG | GCTGCCAGGG | GCTCTGGGAG | GGCTGCCGGC | 60 |
|---|---|---|---|---|---|---|
| AGCCCCGTCC | CCCTCCCGCC | CTTGGTTTTA | G | | | 91 |

( 2 ) INFORMATION FOR SEQ ID NO:54:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:54:

| Asn | His | Gln | Ala | Val | Arg | Asn | Pro |
|---|---|---|---|---|---|---|---|
| 1 | | | | 5 | | | |

( 2 ) INFORMATION FOR SEQ ID NO:55:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:55:

```
Asn His Gln Ala Val Arg Asn Pro Arg Glu Arg Leu Pro Gly Ala Leu
 1           5                   10                  15
Gly Gly Leu Pro Ala Ala Pro Ser Pro Ser Arg Pro Trp Phe
            20                  25                  30
```

( 2 ) INFORMATION FOR SEQ ID NO:56:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:56:

CGGAATTCAA GTACTTCATG GTGGGCCA        28

( 2 ) INFORMATION FOR SEQ ID NO:57:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:57:

AAGCACTTCA TGGTGGGCCA        20

( 2 ) INFORMATION FOR SEQ ID NO:58:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:58:

TGGCATGATG AAAGCCATCT                                              20

( 2 ) INFORMATION FOR SEQ ID NO:59:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:59:

ATGTACTTCA TGGTTGGCCA                                              20

( 2 ) INFORMATION FOR SEQ ID NO:60:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:60:

TGGCATGATG AGAGCCACCT                                              20

( 2 ) INFORMATION FOR SEQ ID NO:61:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:61:

AGGTACTTCA TGGTTGGCCA                                              20

( 2 ) INFORMATION FOR SEQ ID NO:62:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:62:

TGGCATGATG AAAGCCACCT
20

( 2 ) INFORMATION FOR SEQ ID NO:63:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:63:

AAGCACTTCA TGGTGGGCCA
20

( 2 ) INFORMATION FOR SEQ ID NO:64:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:64:

TGGCACGACG AGAGCCACCT
20

( 2 ) INFORMATION FOR SEQ ID NO:65:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:65:

ACCGTGCTGC TTTCGGTGGA CTTAAGGC
28

( 2 ) INFORMATION FOR SEQ ID NO:66:

( i ) SEQUENCE CHARACTERISTICS:
        ( A ) LENGTH: 585 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( i x ) FEATURE:
        ( A ) NAME/KEY: CDS
        ( B ) LOCATION: 1..585

( x i ) SEQUENCE DESCRIPTION: SEQ ID NO:66:

| | | | | | |
|---|---|---|---|---|---|
| GTGGCTNNNT | TCCTGAAGCT | GTTCCTGGAG | ACGGCGGAGA | AGCACTTCAT | GGTGGGCCAC | 60 |
| CGTGTCCACT | ACTATGTCTT | CACCGACCAG | CTGGCCGCGG | TGCCCCGCGT | GACGCTGGGG | 120 |
| ACCGGTCGGC | AGCTGTCAGT | GCTGGAGGTG | CGCGCCTACA | AGCGCTGGCA | GGACGTGTCC | 180 |
| ATGCGCCGCA | TGGAGATGAT | CAGTGACTTC | TGCGAGCGGC | GCTTCCTCAG | CGAGGTGGAT | 240 |
| TACCTGGTGT | GCGTGGACGT | GGACATGGAG | TTCCGCGACC | ACGTGGGCGT | GGAGATCCTG | 300 |
| ACTCCGCTGT | TCGGCACCCT | GCACCCCGGC | TTCTACGGAA | GCAGCCGGGA | GGCCTTCACC | 360 |
| TACGAGCGCC | GGCCCCAGTC | CCAGGCCTAC | ATCCCCAAGG | ACGAGGGCGA | TTTCTACTAC | 420 |
| CTGGGGGGGT | TCTTCGGGGG | GTCGGTGCAA | GAGGTGCAGC | GGCTCACCAG | GGCCTGCCAC | 480 |
| CAGGCCATGA | TGGTCGACCA | GGCCAACGGC | ATCGAGGCCG | TGTGGCACGA | CGAGAGCCAC | 540 |
| CTGAACAAGT | ACCTGCTGCG | CCACAAACCC | ACCAAGGTGC | TCTCC | | 585 |

( 2 ) INFORMATION FOR SEQ ID NO:67:

( i ) SEQUENCE CHARACTERISTICS:
        ( A ) LENGTH: 463 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( i x ) FEATURE:
        ( A ) NAME/KEY: CDS
        ( B ) LOCATION: 1..463

( x i ) SEQUENCE DESCRIPTION: SEQ ID NO:67:

| | | | | | |
|---|---|---|---|---|---|
| TAGGGTGAAC | TACTACANCT | TCACCAACCA | GCCAGGACAC | ATTCCACACA | TCAAGCTCTG | 60 |
| AGAGGGACGG | CAGATGGTCA | TCCTCCAGGT | CCAGAGCTAT | GCCCACTGGC | AGGACATCAC | 120 |
| CAGGCACCGC | ATGGAGGTGA | TCAGCAACTT | TTCCCAGCAG | CACTTCCTCG | GGGAGGTGGA | 180 |
| TTACCTTGTG | TGTGCAGATG | TGGACATGAA | GTTCAACAAC | CATGTGGGTG | TGGAGATCCT | 240 |
| CTCTTCCCTG | TTTGCCACCA | TCCATCCTGG | CTTCTATGGG | TTCCATCGGG | ACACCTTTGC | 300 |
| CTATGAATGC | CAGCCTCAGT | CCCAAGCCCA | TTTTCCTGAG | GGTGAAGGGG | ACTTTTATTA | 360 |
| TATAGGGGCC | TTATTTGGTG | GGTCAGTGCT | GGAGGTTTAC | AGGCTGATCA | TGGCCTGTCA | 420 |
| CCAGGTGATG | ATGATTGACC | AAGCCAACCA | CATCGAGGCC | CTG | | 463 |

( 2 ) INFORMATION FOR SEQ ID NO:68:

( i ) SEQUENCE CHARACTERISTICS:
        ( A ) LENGTH: 195 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:68:

```
Val Ala Xaa Phe Leu Lys Leu Phe Leu Glu Thr Ala Glu Lys His Phe
 1               5                  10                  15

Met Val Gly His Arg Val His Tyr Tyr Val Phe Thr Asp Gln Pro Ala
                20                  25                  30

Ala Val Pro Arg Val Thr Leu Gly Thr Gly Arg Gln Leu Ser Val Leu
            35                  40                  45

Glu Val Arg Ala Tyr Lys Arg Trp Gln Asp Val Ser Met Arg Arg Met
        50                  55                  60

Glu Met Ile Ser Asp Phe Cys Glu Arg Arg Phe Leu Ser Glu Val Asp
65                  70                  75                  80

Tyr Leu Val Cys Val Asp Val Asp Met Glu Phe Arg Asp His Val Gly
                85                  90                  95

Val Glu Ile Leu Thr Pro Leu Phe Gly Thr Leu His Pro Gly Phe Tyr
            100                 105                 110

Gly Ser Ser Arg Glu Ala Phe Thr Tyr Glu Arg Arg Pro Gln Ser Gln
        115                 120                 125

Ala Tyr Ile Pro Lys Asp Glu Gly Asp Phe Tyr Tyr Leu Gly Gly Phe
    130                 135                 140

Phe Gly Gly Ser Val Gln Glu Val Gln Arg Leu Thr Arg Ala Cys His
145                 150                 155                 160

Gln Ala Met Met Val Asp Gln Ala Asn Gly Ile Glu Ala Val Trp His
                165                 170                 175

Asp Glu Ser His Leu Asn Lys Tyr Leu Leu Arg His Lys Pro Thr Lys
            180                 185                 190

Val Leu Ser
    195
```

( 2 ) INFORMATION FOR SEQ ID NO:69:

( i ) SEQUENCE CHARACTERISTICS:
( A ) LENGTH: 154 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:69:

```
Arg Val Asn Tyr Tyr Xaa Phe Thr Asn Gln Pro Gly His Ile Pro His
 1               5                  10                  15

Ile Lys Leu Xaa Glu Gly Arg Gln Met Val Ile Leu Gln Val Gln Ser
                20                  25                  30

Tyr Ala His Trp Gln Asp Ile Thr Arg His Arg Met Glu Val Ile Ser
            35                  40                  45

Asn Phe Ser Gln Gln His Phe Leu Gly Glu Val Asp Tyr Leu Val Cys
        50                  55                  60

Ala Asp Val Asp Met Lys Phe Asn Asn His Val Gly Val Glu Ile Leu
65                  70                  75                  80

Ser Ser Leu Phe Ala Thr Ile His Pro Gly Phe Tyr Gly Phe His Arg
                85                  90                  95

Asp Thr Phe Ala Tyr Glu Cys Gln Pro Gln Ser Gln Ala His Phe Pro
```

-continued

```
               100                      105                         110
    Glu Gly Glu Gly Asp Phe Tyr Tyr Ile Gly Ala Leu Phe Gly Gly Ser
            115             120                     125

Val Leu Glu Val Tyr Arg Leu Ile Met Val Cys His Gln Val Met Met
        130             135                 140

Ile Asp Gln Ala Asn His Ile Glu Ala Leu
    145                 150
```